United States Patent
Al-Ali et al.

(10) Patent No.: US 10,154,815 B2
(45) Date of Patent: Dec. 18, 2018

(54) MODULAR PHYSIOLOGICAL SENSORS

(71) Applicant: MASIMO CORPORATION, Irvine, CA (US)

(72) Inventors: Ammar Al-Ali, San Juan Capistrano, CA (US); Kevin Forrest, Rancho Santa Margarita, CA (US)

(73) Assignee: Masimo Corporation, Irvine, CA (US)

(*) Notice: Subject to any disclaimer, the term of this patent is extended or adjusted under 35 U.S.C. 154(b) by 478 days.

(21) Appl. No.: 14/876,307

(22) Filed: Oct. 6, 2015

(65) Prior Publication Data
US 2016/0095548 A1    Apr. 7, 2016

Related U.S. Application Data

(60) Provisional application No. 62/061,132, filed on Oct. 7, 2014.

(51) Int. Cl.
*A61B 5/00*   (2006.01)
*A61B 5/1455*   (2006.01)
(Continued)

(52) U.S. Cl.
CPC .......... *A61B 5/6814* (2013.01); *A61B 5/0476* (2013.01); *A61B 5/0478* (2013.01);
(Continued)

(58) Field of Classification Search
CPC ... A61B 5/6814; A61B 5/0476; A61B 5/0478; A61B 5/1455; A61B 5/14553;
(Continued)

(56) References Cited

U.S. PATENT DOCUMENTS

| 3,638,640 A | 2/1972 | Shaw |
| 4,223,680 A | 9/1980 | Jobsis |

(Continued)

FOREIGN PATENT DOCUMENTS

| EP | 505491 | 9/1992 |
| EP | 0 541 393 | 11/1992 |

(Continued)

OTHER PUBLICATIONS

US 8,845,543, 09/2014, Diab et al. (withdrawn)
(Continued)

*Primary Examiner* — Gary Jackson
*Assistant Examiner* — Zahed Kabir
(74) *Attorney, Agent, or Firm* — Knobbe, Martens, Olson & Bear, LLP

(57) ABSTRACT

Modular physiological sensors that are physically and/or electrically configured to share a measurement site for the comfort of the patient and/or to ensure proper operation of the sensors without interference from the other sensors. The modular aspect is realized by providing outer housing shapes that generally conform to other physiological sensors; mounting areas for attachment of one sensor to another sensor; providing release liners on the overlapping sensor attachment areas; and/or providing notches, tabs or other mechanical features that provide for the proper placement and interaction of the sensors.

22 Claims, 7 Drawing Sheets

(51) Int. Cl.
*A61B 5/0476* (2006.01)
*A61B 5/0478* (2006.01)

(52) U.S. Cl.
CPC ........ *A61B 5/1455* (2013.01); *A61B 5/14553* (2013.01); *A61B 5/684* (2013.01); *A61B 5/6833* (2013.01); *A61B 2560/0443* (2013.01); *A61B 2562/04* (2013.01); *A61B 2562/06* (2013.01); *A61B 2562/16* (2013.01)

(58) Field of Classification Search
CPC .................. A61B 5/6833; A61B 5/684; A61B 2560/0443; A61B 2562/04; A61B 2562/06; A61B 2562/16
USPC .................................................. 600/300, 301
See application file for complete search history.

(56) References Cited

U.S. PATENT DOCUMENTS

| | | |
|---|---|---|
| 4,281,645 A | 8/1981 | Jobsis |
| 4,321,930 A | 3/1982 | Jobsis et al. |
| 4,380,240 A | 4/1983 | Jobsis et al. |
| 4,510,938 A | 4/1985 | Jobsis et al. |
| 4,796,184 A | 1/1989 | Bahr et al. |
| 4,803,997 A | 2/1989 | Bowman |
| 4,805,623 A | 2/1989 | Jobsis |
| 4,901,238 A | 2/1990 | Suzuki et al. |
| 4,907,876 A | 3/1990 | Suzuki et al. |
| 4,908,762 A | 3/1990 | Suzuki et al. |
| 4,917,116 A | 4/1990 | LaViola et al. |
| 4,928,696 A | 5/1990 | Henderson et al. |
| 4,938,218 A | 7/1990 | Goodman et al. |
| 4,957,000 A | 9/1990 | Delpy et al. |
| 4,960,128 A | 10/1990 | Gordon et al. |
| 4,964,408 A | 10/1990 | Hink et al. |
| 4,967,038 A | 10/1990 | Gevins et al. |
| 4,972,331 A | 11/1990 | Chance |
| 4,996,992 A | 3/1991 | LaViola et al. |
| 5,022,403 A | 6/1991 | LaViola |
| 5,032,024 A | 7/1991 | Cope |
| 5,038,782 A | 8/1991 | Gevins et al. |
| 5,041,187 A | 8/1991 | Hink et al. |
| 5,069,213 A | 12/1991 | Polczynski |
| 5,090,415 A | 2/1992 | Yamashita et al. |
| 5,099,842 A | 3/1992 | Mannheimer et al. |
| 5,101,830 A | 4/1992 | Duffy et al. |
| 5,103,829 A | 4/1992 | Suzuki et al. |
| 5,109,849 A | 5/1992 | Goodman et al. |
| 5,119,815 A | 6/1992 | Chance |
| 5,122,974 A | 6/1992 | Chance |
| 5,154,180 A | 10/1992 | Blanchet et al. |
| 5,163,438 A | 11/1992 | Gordon et al. |
| 5,179,570 A | 1/1993 | Imran |
| 5,179,957 A | 1/1993 | Williams |
| 5,181,520 A | 1/1993 | Wertheim et al. |
| 5,187,672 A | 2/1993 | Chance et al. |
| 5,195,531 A | 3/1993 | Bennett |
| 5,211,174 A | 5/1993 | Imran |
| 5,213,105 A | 5/1993 | Gratton et al. |
| 5,218,962 A | 6/1993 | Mannheimer et al. |
| 5,220,502 A | 6/1993 | Qian et al. |
| 5,226,417 A | 7/1993 | Swedlow et al. |
| 5,228,440 A | 7/1993 | Chung et al. |
| 5,233,983 A | 8/1993 | Markowitz |
| 5,247,932 A | 9/1993 | Chung et al. |
| 5,253,646 A | 10/1993 | Delpy et al. |
| 5,280,793 A | 1/1994 | Rosenfeld et al. |
| 5,289,822 A | 3/1994 | Highe et al. |
| 5,295,482 A | 3/1994 | Clare et al. |
| 5,299,118 A | 3/1994 | Martens et al. |
| 5,299,822 A | 4/1994 | Mayr et al. |
| 5,319,355 A | 6/1994 | Russek |
| 5,320,109 A | 6/1994 | Chamoun et al. |
| 5,327,888 A | 7/1994 | Imran |
| 5,331,959 A | 7/1994 | Imran |
| 5,337,744 A | 8/1994 | Branigan |
| 5,337,745 A | 8/1994 | Benaron |
| 5,341,805 A | 8/1994 | Stavridi et al. |
| 5,345,934 A | 9/1994 | Highe et al. |
| 5,353,799 A | 10/1994 | Chance |
| 5,361,773 A | 11/1994 | Ives |
| D353,195 S | 12/1994 | Savage et al. |
| D353,196 S | 12/1994 | Savage et al. |
| 5,377,674 A | 1/1995 | Kuestner |
| 5,377,675 A | 1/1995 | Ruskewicz et al. |
| 5,377,676 A | 1/1995 | Vari et al. |
| 5,381,804 A | 1/1995 | Shambroom |
| 5,386,827 A | 2/1995 | Chance et al. |
| 5,402,778 A | 4/1995 | Chance |
| 5,406,957 A | 4/1995 | Tansey |
| 5,413,098 A | 5/1995 | Benaron |
| D359,546 S | 6/1995 | Savage et al. |
| 5,421,329 A | 6/1995 | Casciani et al. |
| 5,424,843 A | 6/1995 | Tromberg et al. |
| 5,431,170 A | 7/1995 | Mathews |
| 5,435,316 A | 7/1995 | Kruse |
| D361,840 S | 8/1995 | Savage et al. |
| 5,441,054 A | 8/1995 | Tsuchiya |
| D362,063 S | 9/1995 | Savage et al. |
| 5,448,997 A | 9/1995 | Kruse et al. |
| 5,450,855 A | 9/1995 | Rosenfeld et al. |
| 5,452,717 A | 9/1995 | Branigan et al. |
| 5,452,718 A | 9/1995 | Clare et al. |
| D363,120 S | 10/1995 | Savage et al. |
| 5,456,252 A | 10/1995 | Vari et al. |
| 5,458,117 A | 10/1995 | Chamoun et al. |
| 5,477,051 A | 12/1995 | Tsuchiya |
| 5,479,934 A | 1/1996 | Imran |
| 5,482,034 A | 1/1996 | Lewis et al. |
| 5,482,036 A | 1/1996 | Diab et al. |
| 5,483,969 A | 1/1996 | Testerman et al. |
| 5,485,851 A | 1/1996 | Erickson |
| 5,490,505 A | 2/1996 | Diab et al. |
| 5,492,118 A | 2/1996 | Gratton et al. |
| 5,494,043 A | 2/1996 | O'Sullivan et al. |
| 5,497,769 A | 3/1996 | Gratton et al. |
| 5,511,552 A | 4/1996 | Johnson |
| 5,517,987 A | 5/1996 | Tsuchiya |
| 5,520,176 A | 5/1996 | Cohen |
| 5,520,683 A | 5/1996 | Subramaniam et al. |
| 5,522,862 A | 6/1996 | Testerman et al. |
| 5,529,065 A | 6/1996 | Tsuchiya |
| 5,533,511 A | 7/1996 | Kaspari et al. |
| 5,534,851 A | 7/1996 | Russek |
| 5,540,722 A | 7/1996 | Clare et al. |
| 5,540,733 A | 7/1996 | Testerman et al. |
| 5,546,952 A | 8/1996 | Erikson |
| 5,549,655 A | 8/1996 | Erikson |
| 5,553,614 A | 9/1996 | Chance |
| 5,561,275 A | 10/1996 | Savage et al. |
| 5,562,002 A | 10/1996 | Lalin |
| 5,564,417 A | 10/1996 | Chance |
| 5,564,418 A | 10/1996 | Ozaki et al. |
| 5,582,169 A | 12/1996 | Oda et al. |
| 5,590,649 A | 1/1997 | Caro et al. |
| 5,596,038 A | 1/1997 | Subramaniam |
| 5,596,987 A | 1/1997 | Chance |
| 5,602,924 A | 2/1997 | Durand et al. |
| 5,605,157 A | 2/1997 | Panescu et al. |
| 5,626,145 A | 5/1997 | Clapp et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,247 A | 6/1997 | Tsuchiya et al. |
| 5,645,440 A | 7/1997 | Tobler et al. |
| 5,664,574 A | 9/1997 | Chance |
| 5,673,701 A | 10/1997 | Chance |
| 5,676,142 A | 10/1997 | Miwa et al. |
| 5,678,558 A | 10/1997 | Johnson |
| 5,678,560 A | 10/1997 | Sakamoto et al. |
| 5,685,299 A | 11/1997 | Diab et al. |
| 5,686,516 A | 11/1997 | Tzur |
| 5,694,931 A | 12/1997 | Tsuchiya |

(56) References Cited

U.S. PATENT DOCUMENTS

| | | |
|---|---|---|
| 5,697,367 A | 12/1997 | Lewis et al. |
| 5,706,821 A | 1/1998 | Matcher et al. |
| 5,711,316 A | 1/1998 | Elsberry et al. |
| 5,713,923 A | 2/1998 | Ward et al. |
| 5,727,547 A | 3/1998 | Levinson et al. |
| D393,830 S | 4/1998 | Tobler et al. |
| 5,743,260 A | 4/1998 | Chung et al. |
| 5,743,262 A | 4/1998 | Lepper, Jr. et al. |
| 5,746,210 A | 5/1998 | Benaron et al. |
| 5,752,519 A | 5/1998 | Benaron et al. |
| 5,752,914 A | 5/1998 | Delonzor et al. |
| 5,755,739 A | 5/1998 | Sun et al. |
| 5,758,644 A | 6/1998 | Diab et al. |
| 5,760,910 A | 6/1998 | Lepper, Jr. et al. |
| 5,765,563 A | 6/1998 | Schaaf et al. |
| 5,769,785 A | 6/1998 | Diab et al. |
| 5,772,587 A | 6/1998 | Gratton et al. |
| 5,772,588 A | 6/1998 | Miwa et al. |
| 5,772,605 A | 6/1998 | Weijand |
| 5,775,330 A | 7/1998 | Kangas et al. |
| 5,776,058 A | 7/1998 | Levinson et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,785,658 A | 7/1998 | Benaron et al. |
| 5,785,659 A | 7/1998 | Caro et al. |
| 5,791,347 A | 8/1998 | Flaherty et al. |
| 5,792,069 A | 8/1998 | Greenwald et al. |
| 5,807,261 A | 9/1998 | Benaron et al. |
| 5,807,263 A | 9/1998 | Chance |
| 5,810,734 A | 9/1998 | Caro et al. |
| 5,813,404 A | 9/1998 | Devlin et al. |
| 5,813,980 A | 9/1998 | Levinson et al. |
| 5,813,993 A | 9/1998 | Kaplan et al. |
| 5,816,247 A | 10/1998 | Maynard |
| 5,820,558 A | 10/1998 | Chance |
| 5,823,950 A | 10/1998 | Diab et al. |
| 5,823,952 A | 10/1998 | Levinson et al. |
| 5,830,131 A | 11/1998 | Caro et al. |
| 5,833,618 A | 11/1998 | Caro et al. |
| 5,833,709 A | 11/1998 | Rise et al. |
| 5,846,208 A | 12/1998 | Pichlmayr et al. |
| 5,851,179 A | 12/1998 | Ritson et al. |
| 5,853,370 A | 12/1998 | Chance et al. |
| RE36,044 E | 1/1999 | Benaron |
| 5,857,979 A | 1/1999 | Ryu et al. |
| 5,860,919 A | 1/1999 | Kiani-Azarbayjany et al. |
| 5,865,736 A | 2/1999 | Baker, Jr. et al. |
| 5,873,821 A | 2/1999 | Chance et al. |
| 5,879,294 A | 3/1999 | Anderson et al. |
| 5,890,929 A | 4/1999 | Mills et al. |
| 5,902,235 A | 5/1999 | Lewis et al. |
| 5,904,654 A | 5/1999 | Wohltmann et al. |
| 5,917,190 A | 6/1999 | Yodh et al. |
| 5,919,134 A | 7/1999 | Diab |
| 5,934,925 A | 8/1999 | Tobler et al. |
| 5,940,182 A | 8/1999 | Lepper, Jr. et al. |
| 5,954,053 A | 9/1999 | Chance et al. |
| 5,975,085 A | 11/1999 | Rise |
| 5,983,121 A | 11/1999 | Tsuchiya |
| 5,987,346 A | 11/1999 | Benaron et al. |
| 5,987,351 A | 11/1999 | Chance |
| 5,995,855 A | 11/1999 | Kiani et al. |
| 5,997,343 A | 12/1999 | Mills et al. |
| 5,999,846 A | 12/1999 | Pardey et al. |
| 6,002,952 A | 12/1999 | Diab et al. |
| 6,011,986 A | 1/2000 | Diab et al. |
| 6,011,990 A | 1/2000 | Schultz et al. |
| 6,077,223 A | 1/2000 | Satherley |
| 6,027,452 A | 2/2000 | Flaherty et al. |
| 6,032,064 A | 2/2000 | Devlin et al. |
| 6,032,065 A | 2/2000 | Brown et al. |
| 6,032,072 A | 2/2000 | Greenwald et al. |
| 6,035,223 A | 3/2000 | Baker, Jr. |
| 6,036,642 A | 3/2000 | Diab et al. |
| 6,041,783 A | 3/2000 | Gruenke |
| 6,045,509 A | 4/2000 | Caro et al. |
| 6,052,619 A | 4/2000 | John |
| 6,058,324 A | 5/2000 | Chance |
| 6,058,331 A | 5/2000 | King |
| 6,067,462 A | 5/2000 | Diab et al. |
| 6,067,467 A | 5/2000 | John |
| 6,069,975 A | 5/2000 | Lehmann et al. |
| 6,070,098 A | 5/2000 | Moore-Ede et al. |
| 6,075,610 A | 6/2000 | Ueda et al. |
| 6,076,010 A | 6/2000 | Boas et al. |
| 6,078,833 A | 6/2000 | Hueber |
| 6,081,735 A | 6/2000 | Diab et al. |
| 6,088,607 A | 7/2000 | Diab et al. |
| 6,108,571 A | 8/2000 | Minoz et al. |
| 6,109,269 A | 8/2000 | Rise et al. |
| 6,110,522 A | 8/2000 | Lepper, Jr. et al. |
| 6,115,622 A | 9/2000 | Minoz |
| 6,119,029 A | 9/2000 | Williams |
| 6,124,597 A | 9/2000 | Shehada |
| 6,128,520 A | 10/2000 | Minoz |
| 6,128,521 A | 10/2000 | Marro et al. |
| 6,129,675 A | 10/2000 | Jay |
| 6,141,574 A | 11/2000 | Satherley et al. |
| 6,142,938 A | 11/2000 | Satherley |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,154,669 A | 11/2000 | Hunter et al. |
| 6,157,850 A | 12/2000 | Diab et al. |
| 6,157,857 A | 12/2000 | Dimpfel |
| 6,165,005 A | 12/2000 | Mills et al. |
| 6,176,242 B1 | 1/2001 | Rise |
| 6,184,521 B1 | 2/2001 | Coffin, IV et al. |
| 6,192,260 B1 | 2/2001 | Chance |
| 6,192,261 B1 | 2/2001 | Gratton et al. |
| 6,200,264 B1 | 3/2001 | Satherley et al. |
| 6,206,830 B1 | 3/2001 | Diab et al. |
| 6,216,021 B1 | 4/2001 | Franceschini et al. |
| 6,227,203 B1 | 5/2001 | Rise et al. |
| 6,229,856 B1 | 5/2001 | Diab et al. |
| 6,232,609 B1 | 5/2001 | Snyder et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,236,874 B1 | 5/2001 | Devlin et al. |
| 6,236,885 B1 | 5/2001 | Hunter et al. |
| 6,240,305 B1 | 5/2001 | Tsuchiya |
| 6,241,683 B1 | 6/2001 | Macklem et al. |
| 6,245,013 B1 | 6/2001 | Minoz et al. |
| 6,246,892 B1 | 6/2001 | Chance |
| 6,251,126 B1 | 6/2001 | Ottenhoff et al. |
| 6,253,097 B1 | 6/2001 | Aronow et al. |
| 6,256,523 B1 | 7/2001 | Diab et al. |
| 6,263,221 B1 | 7/2001 | Chance et al. |
| 6,263,222 B1 | 7/2001 | Diab et al. |
| 6,263,237 B1 | 7/2001 | Rise |
| 6,269,269 B1 | 7/2001 | Ottenhoff et al. |
| 6,272,363 B1 | 8/2001 | Casciani et al. |
| 6,272,367 B1 | 8/2001 | Chance |
| 6,272,378 B1 | 8/2001 | Baumgart-Schmitt |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,298,252 B1 | 10/2001 | Kovach et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,335,792 B1 | 1/2002 | Tsuchiya |
| 6,337,997 B1 | 1/2002 | Rise |
| 6,338,713 B1 | 1/2002 | Chamoun et al. |
| 6,343,224 B1 | 1/2002 | Parker |
| 6,343,229 B1 | 1/2002 | Siebler et al. |
| 6,349,228 B1 | 2/2002 | Kiani et al. |
| 6,356,784 B1 | 3/2002 | Lozano et al. |
| 6,360,114 B1 | 3/2002 | Diab et al. |

(56) References Cited

U.S. PATENT DOCUMENTS

| | | |
|---|---|---|
| 6,368,283 B1 | 4/2002 | Xu et al. |
| 6,368,287 B1 | 4/2002 | Hadas |
| 6,371,921 B1 | 4/2002 | Caro et al. |
| 6,374,140 B1 | 4/2002 | Rise |
| 6,377,829 B1 | 4/2002 | Al-Ali |
| 6,377,840 B1 | 4/2002 | Gritsenko et al. |
| 6,385,486 B1 | 5/2002 | John et al. |
| 6,388,240 B2 | 5/2002 | Schulz et al. |
| 6,397,091 B2 | 5/2002 | Diab et al. |
| 6,397,099 B1 | 5/2002 | Chance |
| 6,397,845 B1 | 6/2002 | Burton |
| 6,416,480 B1 | 7/2002 | Nenov |
| 6,430,437 B1 | 8/2002 | Marro |
| 6,430,525 B1 | 8/2002 | Weber et al. |
| 6,456,862 B2 | 9/2002 | Benni |
| 6,463,310 B1 | 10/2002 | Swedlow et al. |
| 6,463,311 B1 | 10/2002 | Diab |
| 6,470,199 B1 | 10/2002 | Kopotic et al. |
| 6,473,632 B1 | 10/2002 | Myers |
| 6,481,899 B1 | 11/2002 | Quast et al. |
| 6,487,343 B1 | 11/2002 | Lewandowski et al. |
| 6,496,724 B1 | 12/2002 | Levendowski et al. |
| 6,497,658 B2 | 12/2002 | Roizen et al. |
| 6,501,975 B2 | 12/2002 | Diab et al. |
| 6,505,059 B1 | 1/2003 | Kollias et al. |
| 6,511,424 B1 | 1/2003 | Moore-Ede et al. |
| 6,515,273 B2 | 2/2003 | Al-Ali |
| 6,516,209 B2 | 2/2003 | Cheng et al. |
| 6,516,214 B1 | 2/2003 | Boas |
| 6,519,487 B1 | 2/2003 | Parker |
| 6,525,386 B1 | 2/2003 | Mills et al. |
| 6,526,300 B1 | 2/2003 | Kiani et al. |
| 6,526,309 B1 | 2/2003 | Chance |
| 6,537,228 B1 | 3/2003 | Lambert |
| 6,541,756 B2 | 4/2003 | Schulz et al. |
| 6,542,764 B1 | 4/2003 | Al-Ali et al. |
| 6,542,772 B1 | 4/2003 | Chance |
| 6,549,284 B1 | 4/2003 | Boas et al. |
| 6,564,076 B1 | 5/2003 | Chance |
| 6,567,165 B1 | 5/2003 | Tsuchiya et al. |
| 6,572,542 B1 | 6/2003 | Houben et al. |
| 6,575,902 B1 | 6/2003 | Burton |
| 6,577,884 B1 | 6/2003 | Boas |
| 6,580,086 B1 | 6/2003 | Schulz et al. |
| 6,584,336 B1 | 6/2003 | Ali et al. |
| 6,587,703 B2 | 7/2003 | Cheng et al. |
| 6,591,123 B2 | 7/2003 | Fein et al. |
| 6,594,513 B1 | 7/2003 | Jobsis et al. |
| 6,594,518 B1 | 7/2003 | Benaron et al. |
| 6,595,316 B2 | 7/2003 | Cybulski et al. |
| 6,597,931 B1 | 7/2003 | Cheng et al. |
| 6,597,932 B2 | 7/2003 | Tian et al. |
| 6,597,933 B2 | 7/2003 | Kiani et al. |
| 6,597,944 B1 | 7/2003 | Hadas |
| 6,599,281 B1 | 7/2003 | Struys et al. |
| 6,605,072 B2 | 8/2003 | Struys et al. |
| 6,606,511 B1 | 8/2003 | Ali et al. |
| 6,609,024 B1 | 8/2003 | Ryu et al. |
| 6,615,065 B1 | 9/2003 | Barrett et al. |
| 6,618,614 B1 | 9/2003 | Chance |
| 6,631,291 B2 | 10/2003 | Viertio-Oja et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,654,626 B2 | 11/2003 | Devlin et al. |
| 6,654,632 B2 | 11/2003 | Lange et al. |
| 6,658,276 B2 | 12/2003 | Kiani et al. |
| 6,661,161 B1 | 12/2003 | Lanzo et al. |
| 6,662,033 B2 | 12/2003 | Casciani et al. |
| 6,665,560 B2 | 12/2003 | Becker et al. |
| 6,667,803 B1 | 12/2003 | Flessland et al. |
| 6,671,530 B2 | 12/2003 | Chung et al. |
| 6,671,531 B2 | 12/2003 | Al-Ali et al. |
| 6,671,555 B2 | 12/2003 | Gielen et al. |
| 6,675,031 B1 | 1/2004 | Porges et al. |
| 6,678,543 B2 | 1/2004 | Diab et al. |
| 6,684,090 B2 | 1/2004 | Ali et al. |
| 6,684,091 B2 | 1/2004 | Parker |
| 6,687,524 B1 | 2/2004 | Svejk |
| 6,690,959 B2 | 2/2004 | Thompson |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |
| 6,708,048 B1 | 3/2004 | Chance |
| 6,708,049 B1 | 3/2004 | Berson et al. |
| 6,711,426 B2 | 3/2004 | Benaron et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,728,564 B2 | 4/2004 | Lahteenmaki |
| 6,731,975 B1 | 5/2004 | Viertio-Oja |
| 6,735,458 B2 | 5/2004 | Cheng et al. |
| 6,735,459 B2 | 5/2004 | Parker |
| 6,745,060 B2 | 6/2004 | Diab et al. |
| 6,748,259 B1 | 6/2004 | Benaron et al. |
| 6,748,263 B2 | 6/2004 | Griffiths et al. |
| 6,751,499 B2 | 6/2004 | Lange et al. |
| 6,757,558 B2 | 6/2004 | Lange et al. |
| 6,760,607 B2 | 7/2004 | Al-Ali |
| 6,768,920 B2 | 7/2004 | Lange et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,795,724 B2 | 9/2004 | Hogan |
| 6,801,648 B2 | 10/2004 | Cheng |
| 6,801,797 B2 | 10/2004 | Mannheimer et al. |
| 6,801,803 B2 | 10/2004 | Viertio-Oja |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,047 B2 | 12/2004 | Heitmeier et al. |
| 6,830,711 B2 | 12/2004 | Mills et al. |
| 6,836,502 B2 | 12/2004 | Canady et al. |
| 6,839,583 B1 | 1/2005 | Lewandowski et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,871,098 B2 | 5/2005 | Nuttin et al. |
| 6,892,006 B2 | 5/2005 | Lewandowski et al. |
| 6,898,452 B2 | 5/2005 | Al-Ali et al. |
| 6,907,280 B2 | 6/2005 | Becerra et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,934,579 B2 | 8/2005 | Mantzxaridis et al. |
| 6,939,305 B2 | 9/2005 | Flaherty et al. |
| 6,943,348 B1 | 9/2005 | Coffin, IV |
| 6,944,497 B2 | 9/2005 | Stypulkowski |
| 6,950,687 B2 | 9/2005 | Al-Ali |
| 6,950,698 B2 | 9/2005 | Sarkela et al. |
| 6,956,650 B2 | 10/2005 | Boas et al. |
| 6,957,368 B2 | 10/2005 | Neumiller et al. |
| 6,958,815 B2 | 10/2005 | Bevilacqua et al. |
| 6,961,598 B2 | 11/2005 | Diab |
| 6,970,792 B1 | 11/2005 | Diab |
| 6,975,901 B2 | 12/2005 | Philip |
| 6,979,812 B2 | 12/2005 | Al-Ali |
| 6,985,763 B2 | 1/2006 | Boas et al. |
| 6,985,764 B2 | 1/2006 | Mason et al. |
| 6,985,833 B2 | 1/2006 | Shambroom et al. |
| 6,993,371 B2 | 1/2006 | Kiani et al. |
| 6,993,380 B1 | 1/2006 | Modarres |
| 6,996,427 B2 | 2/2006 | Ali et al. |

(56) References Cited

U.S. PATENT DOCUMENTS

| | | |
|---|---|---|
| 6,999,904 B2 | 2/2006 | Weber et al. |
| 7,003,338 B2 | 2/2006 | Weber et al. |
| 7,003,339 B2 | 2/2006 | Diab et al. |
| 7,010,341 B2 | 3/2006 | Chance |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,035,744 B2 | 4/2006 | Cheriet et al. |
| 7,039,449 B2 | 5/2006 | Al-Ali |
| 7,041,060 B2 | 5/2006 | Flaherty et al. |
| 7,044,918 B2 | 5/2006 | Diab |
| 7,047,054 B2 | 5/2006 | Benni |
| 7,047,055 B2 | 5/2006 | Boas et al. |
| 7,047,056 B2 | 5/2006 | Hannula et al. |
| 7,054,680 B1 | 5/2006 | Genger et al. |
| 7,067,893 B2 | 6/2006 | Mills et al. |
| 7,072,701 B2 | 7/2006 | Chen et al. |
| 7,079,977 B2 | 7/2006 | Osorio et al. |
| 7,085,597 B2 | 8/2006 | Fein et al. |
| 7,087,075 B2 | 8/2006 | Briscoe et al. |
| 7,092,748 B2 | 8/2006 | Valdes et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,134,438 B2 | 11/2006 | Makower et al. |
| 7,139,603 B2 | 11/2006 | Chance |
| 7,142,901 B2 | 11/2006 | Kiani et al. |
| 7,146,211 B2 | 12/2006 | Frei et al. |
| 7,149,561 B2 | 12/2006 | Diab |
| 7,149,572 B2 | 12/2006 | Frei et al. |
| 7,162,306 B2 | 1/2007 | Caby et al. |
| 7,167,743 B2 | 1/2007 | Heruth et al. |
| 7,174,206 B2 | 2/2007 | Frei et al. |
| 7,179,279 B2 | 2/2007 | Radons et al. |
| 7,186,966 B2 | 3/2007 | Al-Ali |
| 7,190,261 B2 | 3/2007 | Al-Ali |
| 7,209,861 B2 | 4/2007 | Hively |
| 7,215,984 B2 | 5/2007 | Diab |
| 7,215,986 B2 | 5/2007 | Diab |
| 7,218,964 B2 | 5/2007 | Hill et al. |
| 7,220,240 B2 | 5/2007 | Struys et al. |
| 7,221,971 B2 | 5/2007 | Diab |
| 7,221,975 B2 | 5/2007 | Lindstrom |
| 7,221,979 B2 | 5/2007 | Zhou et al. |
| 7,225,006 B2 | 5/2007 | Al-Ali et al. |
| 7,225,007 B2 | 5/2007 | Al-Ali |
| 7,225,013 B2 | 5/2007 | Geva et al. |
| RE39,672 E | 6/2007 | Shehada et al. |
| 7,228,169 B2 | 6/2007 | Viertio-Oja |
| 7,229,430 B2 | 6/2007 | Hickle et al. |
| 7,231,245 B2 | 6/2007 | Greenwald et al. |
| 7,231,246 B2 | 6/2007 | Rautee et al. |
| 7,232,435 B2 | 6/2007 | Hildebrand et al. |
| 7,239,385 B2 | 7/2007 | Schmitz et al. |
| 7,239,901 B2 | 7/2007 | Gritsenko |
| 7,239,905 B2 | 7/2007 | Kiani-Azarbayjany et al. |
| 7,239,988 B2 | 7/2007 | Hasson et al. |
| 7,242,983 B2 | 7/2007 | Frei et al. |
| 7,245,953 B1 | 7/2007 | Parker |
| 7,248,909 B2 | 7/2007 | Lee et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,254,500 B2 | 8/2007 | Makeig et al. |
| 7,266,412 B2 | 9/2007 | Stypulkowski |
| 7,272,425 B2 | 9/2007 | Al-Ali |
| 7,274,955 B2 | 9/2007 | Kiani et al. |
| D554,263 S | 10/2007 | Al-Ali |
| 7,277,741 B2 | 10/2007 | Debreczeny et al. |
| 7,277,831 B1 | 10/2007 | Pawelzik et al. |
| 7,280,858 B2 | 10/2007 | Al-Ali et al. |
| 7,280,867 B2 | 10/2007 | Frei et al. |
| 7,288,066 B2 | 10/2007 | Drew |
| 7,289,835 B2 | 10/2007 | Mansfield et al. |
| 7,289,837 B2 | 10/2007 | Mannheimer et al. |
| 7,292,883 B2 | 11/2007 | De Felice et al. |
| 7,295,866 B2 | 11/2007 | Al-Ali |
| 7,308,304 B2 | 12/2007 | Hampton et al. |
| 7,313,427 B2 | 12/2007 | Benni |
| 7,328,053 B1 | 2/2008 | Diab et al. |
| 7,332,784 B2 | 2/2008 | Mills et al. |
| 7,333,647 B2 | 2/2008 | Boas et al. |
| 7,340,287 B2 | 3/2008 | Mason et al. |
| 7,341,559 B2 | 3/2008 | Schulz et al. |
| 7,343,186 B2 | 3/2008 | Lamego et al. |
| 7,343,187 B2 | 3/2008 | Stetson |
| 7,349,726 B2 | 3/2008 | Casciani et al. |
| D566,282 S | 4/2008 | Al-Ali et al. |
| 7,355,512 B1 | 4/2008 | Al-Ali |
| 7,355,688 B2 | 4/2008 | Lash et al. |
| 7,356,365 B2 | 4/2008 | Schurman |
| 7,359,837 B2 | 4/2008 | Drew et al. |
| D568,479 S | 5/2008 | Mao et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,373,198 B2 | 5/2008 | Bibian et al. |
| 7,376,453 B1 | 5/2008 | Diab et al. |
| 7,376,454 B2 | 5/2008 | Casciani et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,385,443 B1 | 6/2008 | Denison |
| 7,391,257 B1 | 6/2008 | Denison et al. |
| 7,392,074 B2 | 6/2008 | Isaacson et al. |
| 7,415,297 B2 | 8/2008 | Al-Ali et al. |
| 7,415,298 B2 | 8/2008 | Casciani et al. |
| 7,418,290 B2 | 8/2008 | Devlin et al. |
| 7,421,297 B2 | 9/2008 | Giftakis et al. |
| 7,427,165 B2 | 9/2008 | Benaron et al. |
| 7,428,432 B2 | 9/2008 | Ali et al. |
| 7,428,434 B2 | 9/2008 | Tromberg et al. |
| 7,429,938 B1 | 9/2008 | Corndorf |
| 7,438,683 B2 | 10/2008 | Al-Ali et al. |
| 7,440,787 B2 | 10/2008 | Diab |
| 7,454,240 B2 | 11/2008 | Diab et al. |
| 7,457,652 B2 | 11/2008 | Porges et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,474,245 B1 | 1/2009 | Wang et al. |
| 7,474,247 B1 | 1/2009 | Heinks et al. |
| 7,478,108 B2 | 1/2009 | Townsend et al. |
| 7,479,910 B1 | 1/2009 | Heinks et al. |
| 7,483,729 B2 | 1/2009 | Al-Ali et al. |
| 7,483,730 B2 | 1/2009 | Diab et al. |
| 7,483,731 B2 | 1/2009 | Hoarau et al. |
| 7,486,977 B2 | 2/2009 | Sweitzer et al. |
| 7,489,958 B2 | 2/2009 | Diab et al. |
| 7,496,391 B2 | 2/2009 | Diab et al. |
| 7,496,393 B2 | 2/2009 | Diab et al. |
| 7,496,400 B2 | 2/2009 | Hoskonen et al. |
| D587,657 S | 3/2009 | Al-Ali et al. |
| 7,499,740 B2 | 3/2009 | Nordstrom et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,515,948 B1 | 4/2009 | Balberg et al. |
| 7,522,949 B2 | 4/2009 | Berson et al. |
| 7,526,328 B2 | 4/2009 | Diab et al. |
| 7,526,335 B2 | 4/2009 | Ferek-Petric |
| 7,526,340 B2 | 4/2009 | Drew |
| 7,530,942 B1 | 5/2009 | Diab |
| 7,530,949 B2 | 5/2009 | Al Ali et al. |
| 7,530,955 B2 | 5/2009 | Diab et al. |
| 7,542,803 B2 | 6/2009 | Heruth et al. |
| 7,563,110 B2 | 7/2009 | Al-Ali et al. |
| 7,590,455 B2 | 9/2009 | Heruth et al. |

(56) References Cited

U.S. PATENT DOCUMENTS

| | | |
|---|---|---|
| 7,594,889 B2 | 9/2009 | Ores et al. |
| 7,596,398 B2 | 9/2009 | Al-Ali et al. |
| 7,610,082 B2 | 10/2009 | Chance |
| 7,610,083 B2 | 10/2009 | Drew et al. |
| 7,618,375 B2 | 11/2009 | Flaherty |
| 7,623,053 B2 | 11/2009 | Terry et al. |
| D606,659 S | 12/2009 | Kiani et al. |
| 7,647,083 B2 | 1/2010 | Al-Ali et al. |
| D609,193 S | 2/2010 | Al-Ali et al. |
| 7,684,872 B2 | 3/2010 | Carney et al. |
| D614,305 S | 4/2010 | Al-Ali et al. |
| 7,698,002 B2 | 4/2010 | Music et al. |
| 7,706,871 B2 | 4/2010 | Devlin et al. |
| 7,706,889 B2 | 4/2010 | Gerber et al. |
| 7,706,896 B2 | 4/2010 | Music et al. |
| RE41,317 E | 5/2010 | Parker |
| 7,714,757 B2 | 5/2010 | Denison et al. |
| 7,715,919 B2 | 5/2010 | Osorio et al. |
| 7,717,932 B2 | 5/2010 | McFarlin et al. |
| 7,729,733 B2 | 6/2010 | Al-Ali et al. |
| 7,729,773 B2 | 6/2010 | Sloan |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,761,145 B2 | 7/2010 | Virag et al. |
| 7,761,146 B2 | 7/2010 | Carlson et al. |
| 7,764,982 B2 | 7/2010 | Dalke et al. |
| 7,764,988 B2 | 7/2010 | Drew et al. |
| 7,764,989 B2 | 7/2010 | Carlson et al. |
| D621,516 S | 8/2010 | Kiani et al. |
| 7,769,464 B2 | 8/2010 | Gerber et al. |
| 7,775,993 B2 | 8/2010 | Heruth et al. |
| 7,791,155 B2 | 9/2010 | Diab |
| 7,792,583 B2 | 9/2010 | Miesel et al. |
| 7,801,581 B2 | 9/2010 | Diab |
| 7,805,196 B2 | 9/2010 | Miesel et al. |
| 7,809,434 B2 | 10/2010 | Kofol et al. |
| 7,819,909 B2 | 10/2010 | Goetz et al. |
| 7,822,452 B2 | 10/2010 | Schurman et al. |
| 7,822,481 B2 | 10/2010 | Gerber et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,853,322 B2 | 12/2010 | Bourget et al. |
| 7,865,222 B2 | 1/2011 | Weber et al. |
| 7,865,244 B2 | 1/2011 | Giftakis et al. |
| 7,873,497 B2 | 1/2011 | Weber et al. |
| 7,957,797 B2 | 1/2011 | Bourget et al. |
| 7,880,606 B2 | 2/2011 | Al-Ali |
| 7,880,626 B2 | 2/2011 | Al-Ali et al. |
| 7,881,798 B2 | 2/2011 | Miesel et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,904,168 B2 | 3/2011 | Corndorf |
| 7,909,772 B2 | 3/2011 | Popov et al. |
| 7,910,875 B2 | 3/2011 | Al-Ali |
| 7,912,537 B2 | 3/2011 | Lee et al. |
| 7,917,199 B2 | 3/2011 | Drew et al. |
| 7,935,935 B2 | 3/2011 | Roberts et al. |
| 7,953,492 B2 | 3/2011 | Corndorf |
| 7,919,713 B2 | 4/2011 | Al-Ali et al. |
| 7,925,511 B2 | 4/2011 | Li et al. |
| 7,933,646 B2 | 4/2011 | Frei et al. |
| 7,933,658 B2 | 4/2011 | Corndorf |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,944,551 B2 | 5/2011 | Addison et al. |
| 7,951,086 B2 | 5/2011 | Flaherty et al. |
| 7,957,780 B2 | 6/2011 | Lamego et al. |
| 7,957,799 B2 | 6/2011 | Sullivan et al. |
| 7,957,809 B2 | 6/2011 | Bourget et al. |
| 7,957,812 B2 | 6/2011 | Corndorf |
| 7,962,188 B2 | 6/2011 | Kiani et al. |
| 7,962,190 B1 | 6/2011 | Diab et al. |
| 7,976,472 B2 | 7/2011 | Kiani |
| 7,979,130 B2 | 7/2011 | Carlson et al. |
| 7,983,757 B2 | 7/2011 | Miyazawa et al. |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,000,788 B2 | 8/2011 | Giftakis et al. |
| 8,005,534 B2 | 8/2011 | Greenwald et al. |
| 8,008,088 B2 | 8/2011 | Bellott et al. |
| RE42,753 E | 9/2011 | Kiani-Azarbayjany et al. |
| 8,016,776 B2 | 9/2011 | Bourget et al. |
| 8,016,846 B2 | 9/2011 | McFarlin et al. |
| 8,019,400 B2 | 9/2011 | Diab et al. |
| 8,021,299 B2 | 9/2011 | Miesel et al. |
| 8,024,029 B2 | 9/2011 | Drew et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,050,751 B2 | 11/2011 | Zhang et al. |
| 8,055,348 B2 | 11/2011 | Heruth et al. |
| 8,099,170 B2 | 1/2012 | Jensen et al. |
| 8,103,328 B2 | 1/2012 | Turner et al. |
| 8,108,033 B2 | 1/2012 | Drew et al. |
| 8,108,038 B2 | 1/2012 | Giftakis et al. |
| 8,209,009 B2 | 1/2012 | Giftakis et al. |
| RE43,169 E | 2/2012 | Parker |
| 8,112,148 B2 | 2/2012 | Giftakis et al. |
| 8,112,153 B2 | 2/2012 | Giftakis et al. |
| 8,118,620 B2 | 2/2012 | Al-Ali et al. |
| 8,121,694 B2 | 2/2012 | Molnar et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,135,473 B2 | 3/2012 | Miesel et al. |
| 8,145,287 B2 | 3/2012 | Diab et al. |
| 8,150,487 B2 | 4/2012 | Diab et al. |
| 8,160,683 B2 | 4/2012 | Shah et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,187,181 B2 | 5/2012 | Osorio et al. |
| 8,190,223 B2 | 5/2012 | Al-Ali et al. |
| 8,190,227 B2 | 5/2012 | Diab et al. |
| 8,190,251 B2 | 5/2012 | Molnar et al. |
| 8,200,340 B2 | 6/2012 | Skelton et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,209,018 B2 | 6/2012 | Osorio et al. |
| 8,209,019 B2 | 6/2012 | Giftakis et al. |
| 8,209,029 B2 | 6/2012 | Gray et al. |
| 8,214,035 B2 | 7/2012 | Giftakis et al. |
| 8,219,172 B2 | 7/2012 | Schurman et al. |
| 8,219,206 B2 | 7/2012 | Skelton et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,229,559 B2 | 7/2012 | Westendorp et al. |
| 8,231,556 B2 | 7/2012 | Skelton et al. |
| 8,233,955 B2 | 7/2012 | Al-Ali et al. |
| 8,244,325 B2 | 8/2012 | Al-Ali et al. |
| 8,244,339 B2 | 8/2012 | Shen et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |

(56) References Cited

U.S. PATENT DOCUMENTS

| | | |
|---|---|---|
| 8,265,723 B1 | 9/2012 | McHale et al. |
| 8,265,769 B2 | 9/2012 | Denison |
| 8,274,360 B2 | 9/2012 | Sampath et al. |
| 8,287,451 B2 | 10/2012 | Hu et al. |
| 8,287,520 B2 | 10/2012 | Drew et al. |
| 8,290,596 B2 | 10/2012 | Wei et al. |
| 8,301,217 B2 | 10/2012 | Al-Ali et al. |
| 8,301,233 B2 | 10/2012 | Zhang et al. |
| 8,306,596 B2 | 11/2012 | Schurman et al. |
| 8,308,661 B2 | 11/2012 | Miesel et al. |
| 8,310,336 B2 | 11/2012 | Muhsin et al. |
| 8,315,683 B2 | 11/2012 | Al-Ali et al. |
| 8,315,709 B2 | 11/2012 | Corndorf |
| RE43,860 E | 12/2012 | Parker |
| 8,326,418 B2 | 12/2012 | Sommer et al. |
| 8,326,431 B2 | 12/2012 | Werder et al. |
| 8,332,041 B2 | 12/2012 | Skelton et al. |
| 8,337,403 B2 | 12/2012 | Al-Ali et al. |
| 8,340,769 B2 | 12/2012 | Receveur et al. |
| 8,346,190 B2 | 1/2013 | Corndorf |
| 8,346,330 B2 | 1/2013 | Lamego |
| 8,352,039 B2 | 1/2013 | Davis et al. |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,359,094 B2 | 1/2013 | Bonner et al. |
| 8,364,223 B2 | 1/2013 | Al-Ali et al. |
| 8,364,226 B2 | 1/2013 | Diab et al. |
| 8,364,272 B2 | 1/2013 | Goetz |
| 8,473,063 B2 | 1/2013 | Gupta et al. |
| 8,374,665 B2 | 2/2013 | Lamego |
| 8,376,943 B2 | 2/2013 | Kovach et al. |
| 8,380,314 B2 | 2/2013 | Panken et al. |
| 8,385,995 B2 | 2/2013 | Al-Ali et al. |
| 8,385,996 B2 | 2/2013 | Smith et al. |
| 8,386,053 B2 | 2/2013 | Kornet |
| 8,388,353 B2 | 3/2013 | Kiani et al. |
| 8,388,555 B2 | 3/2013 | Panken et al. |
| 8,396,526 B2 | 3/2013 | Benni |
| 8,399,822 B2 | 3/2013 | Al-Ali |
| 8,400,290 B2 | 3/2013 | Baker et al. |
| 8,401,602 B2 | 3/2013 | Kiani |
| 8,401,666 B2 | 3/2013 | Skelton et al. |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,419,982 B2 | 4/2013 | Copp-Howland et al. |
| 8,423,106 B2 | 4/2013 | Lamego et al. |
| 8,428,674 B2 | 4/2013 | Duffy et al. |
| 8,428,675 B2 | 4/2013 | McKenna |
| 8,428,733 B2 | 4/2013 | Carlson et al. |
| 8,428,744 B2 | 4/2013 | Stancer et al. |
| 8,428,967 B2 | 4/2013 | Olsen et al. |
| 8,430,817 B1 | 4/2013 | Al-Ali et al. |
| 8,406,890 B2 | 5/2013 | Goetz |
| 8,437,825 B2 | 5/2013 | Dalvi et al. |
| 8,447,406 B2 | 5/2013 | Wu et al. |
| 8,452,364 B2 | 5/2013 | Hannula et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,485,979 B2 | 7/2013 | Giftakis et al. |
| 8,489,196 B2 | 7/2013 | Miesel et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,515,510 B2 | 8/2013 | MacLaughlin |
| 8,515,550 B2 | 8/2013 | Skelton et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| 8,532,757 B2 | 9/2013 | Molnar et al. |
| 8,538,513 B2 | 9/2013 | Molnar et al. |
| 8,538,705 B2 | 9/2013 | Greenwald |
| 8,543,214 B2 | 9/2013 | Osorio et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,548,557 B2 | 10/2013 | Garstka et al. |
| 8,554,331 B2 | 10/2013 | Gerber et al. |
| 8,560,032 B2 | 10/2013 | Al-Ali et al. |
| 8,560,034 B1 | 10/2013 | Diab et al. |
| 8,560,064 B2 | 10/2013 | Bonner et al. |
| 8,565,886 B2 | 10/2013 | Nelson et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,577,440 B2 | 11/2013 | Afanasewicz et al. |
| 8,578,082 B2 | 11/2013 | Medina et al. |
| 8,579,786 B2 | 11/2013 | Osorio et al. |
| 8,579,834 B2 | 11/2013 | Davis et al. |
| 8,581,732 B2 | 11/2013 | Al-Ali et al. |
| 8,588,880 B2 | 11/2013 | Abdul-Hafiz et al. |
| 8,594,779 B2 | 11/2013 | Denison et al. |
| 8,594,798 B2 | 11/2013 | Osorio et al. |
| 8,600,467 B2 | 12/2013 | Al-Ali et al. |
| 8,606,342 B2 | 12/2013 | Diab |
| 8,615,299 B2 | 12/2013 | Goetz |
| 8,617,152 B2 | 12/2013 | Werneth et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,660,799 B2 | 2/2014 | Watson et al. |
| 8,663,107 B2 | 3/2014 | Kiani |
| 8,666,468 B1 | 3/2014 | Al-Ali |
| 8,666,505 B2 | 3/2014 | O'Brien et al. |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,671,237 B2 | 3/2014 | Ma et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,185 B2 | 4/2014 | Scholl et al. |
| 8,690,799 B2 | 4/2014 | Telfort et al. |
| 8,700,112 B2 | 4/2014 | Kiani |
| 8,700,122 B2 | 4/2014 | Cordero et al. |
| 8,702,627 B2 | 4/2014 | Telfort et al. |
| 8,706,179 B2 | 4/2014 | Parker |
| 8,706,181 B2 | 4/2014 | Stypulkowski et al. |
| 8,708,934 B2 | 4/2014 | Skelton et al. |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,725,244 B2 | 5/2014 | Miesel et al. |
| 8,728,059 B2 | 5/2014 | Karst et al. |
| 8,740,792 B1 | 6/2014 | Kiani et al. |
| 8,744,587 B2 | 6/2014 | Miesel et al. |
| 8,754,776 B2 | 6/2014 | Poeze et al. |
| 8,755,535 B2 | 6/2014 | Telfort et al. |
| 8,755,856 B2 | 6/2014 | Diab et al. |

(56) References Cited

U.S. PATENT DOCUMENTS

| | | |
|---|---|---|
| 8,755,871 B2 | 6/2014 | Weng et al. |
| 8,755,872 B1 | 6/2014 | Marinow |
| 8,761,850 B2 | 6/2014 | Lamego |
| 8,761,890 B2 | 6/2014 | Gupta et al. |
| 8,764,671 B2 | 7/2014 | Kiani |
| 8,768,423 B2 | 7/2014 | Shakespeare et al. |
| 8,768,446 B2 | 7/2014 | Drew et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,991 B2 | 7/2014 | Gerber et al. |
| 8,798,708 B2 | 8/2014 | Tremblay |
| 8,798,764 B2 | 8/2014 | Molnar et al. |
| 8,801,613 B2 | 8/2014 | Al-Ali et al. |
| 8,805,465 B2 | 8/2014 | Hodge et al. |
| 8,805,528 B2 | 8/2014 | Corndorf |
| 8,805,537 B1 | 8/2014 | Cong et al. |
| 8,812,098 B2 | 8/2014 | Giftakis et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,838,254 B2 | 9/2014 | McClure et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,095 B2 | 10/2014 | Schlottau et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,868,173 B2 | 10/2014 | Nelson et al. |
| 8,868,212 B2 | 10/2014 | Gray |
| 8,870,792 B2 | 10/2014 | Al-Ali et al. |
| 8,880,576 B2 | 11/2014 | Ochs et al. |
| 8,886,271 B2 | 11/2014 | Kiani et al. |
| 8,886,323 B2 | 11/2014 | Wu et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,892,207 B2 | 11/2014 | Nelson et al. |
| 8,897,847 B2 | 11/2014 | Al-Ali |
| 8,898,037 B2 | 11/2014 | Watson et al. |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,914,115 B2 | 12/2014 | Giftakis et al. |
| 8,914,119 B2 | 12/2014 | Wu et al. |
| 8,918,176 B2 | 12/2014 | Nelson et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,922,788 B2 | 12/2014 | Addison et al. |
| 8,929,964 B2 | 1/2015 | Al-Ali et al. |
| 8,936,630 B2 | 1/2015 | Denison et al. |
| 8,941,523 B1 | 1/2015 | Shen et al. |
| 8,942,777 B2 | 1/2015 | Diab et al. |
| 8,948,834 B2 | 2/2015 | Diab et al. |
| 8,948,835 B2 | 2/2015 | Diab |
| 8,958,870 B2 | 2/2015 | Gerber et al. |
| 8,965,471 B2 | 2/2015 | Lamego |
| 8,983,564 B2 | 3/2015 | Al-Ali |
| 8,986,207 B2 | 3/2015 | Li et al. |
| 8,989,831 B2 | 3/2015 | Al-Ali et al. |
| 8,996,085 B2 | 3/2015 | Kiani et al. |
| 8,998,809 B2 | 4/2015 | Kiani |
| 9,008,788 B2 | 4/2015 | Jenison |
| 9,028,429 B2 | 5/2015 | Telfort et al. |
| 9,037,207 B2 | 5/2015 | Al-Ali et al. |
| 9,050,471 B2 | 6/2015 | Skelton et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,072,870 B2 | 7/2015 | Wu et al. |
| 9,077,030 B2 | 7/2015 | Norton et al. |
| 9,078,560 B2 | 7/2015 | Schurman et al. |
| 9,079,039 B2 | 7/2015 | Carlson et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,830 B2 | 8/2015 | Galen et al. |
| 9,113,831 B2 | 8/2015 | Al-Ali |
| 9,113,832 B2 | 8/2015 | Al-Ali |
| 9,119,595 B2 | 9/2015 | Lamego |
| 9,119,597 B2 | 9/2015 | Dripps et al. |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,900 B2 | 9/2015 | Afanasewicz et al. |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,183 B2 | 9/2015 | McKenna et al. |
| 9,138,192 B2 | 9/2015 | Weber et al. |
| 9,142,117 B2 | 9/2015 | Muhsin et al. |
| 9,149,635 B2 | 10/2015 | Denison et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,173,609 B2 | 11/2015 | Nelson |
| 9,176,141 B2 | 11/2015 | Al-Ali et al. |
| 9,179,876 B2 | 11/2015 | Ochs et al. |
| 9,186,102 B2 | 11/2015 | Bruinsma et al. |
| 9,186,519 B2 | 11/2015 | Kivi |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,204,794 B2 | 12/2015 | Lisogurski et al. |
| 9,209,824 B2 | 12/2015 | Shen et al. |
| 9,211,072 B2 | 12/2015 | Kiani |
| 9,211,095 B1 | 12/2015 | Al-Ali |
| 9,211,411 B2 | 12/2015 | Wu et al. |
| 9,218,454 B2 | 12/2015 | Kiani et al. |
| 9,220,409 B2 | 12/2015 | Lisogurski |
| 9,220,436 B2 | 12/2015 | Sandmore et al. |
| 9,226,696 B2 | 1/2016 | Kiani |
| 9,226,709 B2 | 1/2016 | Montague |
| 9,241,662 B2 | 1/2016 | Al-Ali et al. |
| 9,245,668 B1 | 1/2016 | Vo et al. |
| 9,247,896 B2 | 2/2016 | Dripps et al. |
| 9,259,160 B2 | 2/2016 | Watson et al. |
| 9,259,185 B2 | 2/2016 | Abdul-Hafiz et al. |
| 9,267,572 B2 | 2/2016 | Barker et al. |
| 9,267,875 B2 | 2/2016 | Yap et al. |
| 9,277,880 B2 | 3/2016 | Poeze et al. |
| 9,289,136 B2 | 3/2016 | Addison et al. |
| 9,289,167 B2 | 3/2016 | Diab et al. |
| 9,295,421 B2 | 3/2016 | Kiani et al. |
| 9,348,974 B2 | 3/2016 | Goetz |
| 9,307,928 B1 | 4/2016 | Al-Ali et al. |
| 9,314,168 B2 | 4/2016 | Watson et al. |
| 9,323,894 B2 | 4/2016 | Kiani |
| D755,392 S | 5/2016 | Hwang et al. |
| 9,326,712 B1 | 5/2016 | Kiani |
| 9,327,070 B2 | 5/2016 | Skelton et al. |
| 9,333,316 B2 | 5/2016 | Kiani |
| 9,333,350 B2 | 5/2016 | Rise et al. |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,351,688 B2 | 5/2016 | Iyer et al. |
| 9,357,934 B2 | 6/2016 | Watson et al. |
| 9,357,949 B2 | 6/2016 | Drew |

(56) References Cited

U.S. PATENT DOCUMENTS

| | | |
|---|---|---|
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 2002/0019588 A1 | 2/2002 | Marro et al. |
| 2002/0029005 A1 | 3/2002 | Levendowski et al. |
| 2002/0082513 A1 | 6/2002 | Ennen et al. |
| 2002/0085174 A1 | 7/2002 | Bolger et al. |
| 2002/0091335 A1 | 7/2002 | John et al. |
| 2002/0123693 A1 | 9/2002 | Lange et al. |
| 2002/0183634 A1 | 12/2002 | Rantala et al. |
| 2002/0188216 A1 | 12/2002 | Kayyali et al. |
| 2003/0145854 A1 | 8/2003 | Hickle |
| 2003/0158587 A1 | 8/2003 | Esteller et al. |
| 2003/0204148 A1 | 10/2003 | Lange et al. |
| 2003/0069516 A1 | 12/2003 | Becker et al. |
| 2003/0225323 A1* | 12/2003 | Kiani ............ A61B 5/0478 600/323 |
| 2004/0030258 A1 | 2/2004 | Williams et al. |
| 2004/0073098 A1 | 4/2004 | Geva et al. |
| 2004/0073129 A1 | 4/2004 | Caldwell et al. |
| 2004/0082862 A1 | 4/2004 | Chance |
| 2004/0082876 A1 | 4/2004 | Viertio-Oja et al. |
| 2004/0167418 A1 | 8/2004 | Nguyen et al. |
| 2004/0193068 A1 | 9/2004 | Burton et al. |
| 2004/0243017 A1 | 12/2004 | Causevic |
| 2004/0267153 A1 | 12/2004 | Bergethon |
| 2005/0010116 A1 | 1/2005 | Korhonen et al. |
| 2005/0059899 A1 | 3/2005 | Merilainen et al. |
| 2005/0081847 A1 | 4/2005 | Lee et al. |
| 2005/0090754 A1 | 4/2005 | Wolff et al. |
| 2005/0113704 A1 | 5/2005 | Lawson et al. |
| 2005/0119547 A1 | 6/2005 | Shastri et al. |
| 2005/0217674 A1 | 10/2005 | Burton et al. |
| 2005/0277819 A1 | 12/2005 | Kiani et al. |
| 2006/0084852 A1 | 4/2006 | Mason et al. |
| 2006/0100538 A1 | 5/2006 | Genger et al. |
| 2006/0116556 A1 | 6/2006 | Duhamel |
| 2006/0167368 A1 | 7/2006 | Sarkela |
| 2006/0189861 A1 | 8/2006 | Chen et al. |
| 2006/0217628 A1 | 9/2006 | Huiku |
| 2006/0235315 A1 | 10/2006 | Akselrod |
| 2006/0241356 A1 | 10/2006 | Flaherty |
| 2006/0241562 A1 | 10/2006 | Erwin et al. |
| 2006/0293608 A1 | 12/2006 | Rothman et al. |
| 2007/0010755 A1 | 1/2007 | Sarkela et al. |
| 2007/0010756 A1 | 1/2007 | Viertio-Oja |
| 2007/0010795 A1 | 1/2007 | Sarkela et al. |
| 2007/0078311 A1* | 4/2007 | Al-Ali ............ A61B 5/14532 600/310 |
| 2007/0185407 A1 | 8/2007 | Xu et al. |
| 2007/0208269 A1 | 9/2007 | Mumford et al. |
| 2007/0244721 A1 | 10/2007 | Sackner-Bernstein et al. |
| 2007/0249952 A1 | 10/2007 | Rubin et al. |
| 2007/0282478 A1 | 12/2007 | Al-Ali et al. |
| 2008/0017800 A1 | 1/2008 | Benni |
| 2008/0200786 A1 | 8/2008 | Berndsen |
| 2008/0221461 A1 | 9/2008 | Zhou et al. |
| 2008/0234597 A1 | 9/2008 | Becker et al. |
| 2008/0255469 A1 | 10/2008 | Shieh et al. |
| 2008/0285029 A1 | 11/2008 | Benni et al. |
| 2008/0294063 A1 | 11/2008 | Bibian et al. |
| 2008/0300469 A1 | 12/2008 | Kuo et al. |
| 2008/0300473 A1 | 12/2008 | Benni |
| 2008/0300474 A1 | 12/2008 | Benni et al. |
| 2009/0018427 A1 | 1/2009 | Causevic et al. |
| 2009/0018429 A1 | 1/2009 | Saliga et al. |
| 2009/0036799 A1 | 2/2009 | Sandhu et al. |
| 2009/0088619 A1 | 4/2009 | Turner et al. |
| 2009/0108205 A1 | 4/2009 | Duffy et al. |
| 2009/0182209 A1 | 7/2009 | Benni |
| 2009/0247924 A1 | 10/2009 | Lamego et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0281403 A1 | 11/2009 | Benni |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0049018 A1 | 2/2010 | Duffy et al. |
| 2010/0063438 A1 | 3/2010 | Bengtsson |
| 2010/0069725 A1 | 3/2010 | Al-Ali |
| 2010/0130840 A1 | 5/2010 | Isaacson |
| 2010/0261979 A1 | 10/2010 | Kiani |
| 2010/0317936 A1 | 12/2010 | Al-Ali et al. |
| 2011/0001605 A1 | 1/2011 | Kiani et al. |
| 2011/0082711 A1 | 4/2011 | Poeze et al. |
| 2011/0087083 A1 | 4/2011 | Poeze et al. |
| 2011/0105854 A1 | 5/2011 | Kiani et al. |
| 2011/0172967 A1 | 7/2011 | Al-Ali et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0083673 A1* | 4/2012 | Al-Ali ............ A61B 5/0006 600/301 |
| 2012/0088984 A1 | 4/2012 | Al-Ali et al. |
| 2012/0116175 A1 | 5/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0302894 A1 | 11/2012 | Diab et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0030267 A1* | 1/2013 | Lisogurski ............ A61B 5/0478 600/324 |
| 2013/0045685 A1 | 2/2013 | Kiani |
| 2013/0046204 A1 | 2/2013 | Lamego et al. |
| 2013/0041591 A1 | 3/2013 | Lamego |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |

(56) References Cited

U.S. PATENT DOCUMENTS

| | | |
|---|---|---|
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0012153 A1 | 1/2014 | Greenwald |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275875 A1* | 9/2014 | Su ............... A61B 5/684 600/323 |
| 2014/0275881 A1 | 9/2014 | Lamego et al. |
| 2014/0275893 A1 | 9/2014 | Booker |
| 2014/0288400 A1 | 9/2014 | Diab et al. |
| 2014/0296664 A1 | 10/2014 | Bruinsma et al. |
| 2014/0303459 A1 | 10/2014 | Wada et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011857 A1* | 1/2015 | Henson ............... A61B 5/6831 600/383 |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038812 A1 | 2/2015 | Ayaz et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272496 A1 | 10/2015 | Klappert et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166210 A1 | 6/2016 | Al-Ali |
| 2016/0192869 A1 | 7/2016 | Kiani et al. |
| 2016/0196388 A1 | 7/2016 | Lamego |

(56) References Cited

U.S. PATENT DOCUMENTS

| | | |
|---|---|---|
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0027456 A1 | 2/2017 | Kinast et al. |
| 2017/0042488 A1 | 2/2017 | Muhsin |

FOREIGN PATENT DOCUMENTS

| | | |
|---|---|---|
| EP | 638193 | 2/1995 |
| EP | 1250886 | 10/2002 |
| EP | 1624798 | 11/2004 |
| EP | 1779257 | 5/2007 |
| WO | WO 91/09372 | 6/1991 |
| WO | WO 91/19453 | 12/1991 |
| WO | WO 92/02176 | 2/1992 |
| WO | WO 93/21615 | 10/1993 |
| WO | WO 99/08589 | 2/1999 |
| WO | WO 00/21432 | 4/2000 |
| WO | WO 00/21435 | 4/2000 |
| WO | WO 00/56211 | 9/2000 |
| WO | WO 00/56212 | 9/2000 |
| WO | WO 01/30414 | 5/2001 |
| WO | WO 04/028362 | 4/2004 |
| WO | WO 04/054441 | 7/2004 |
| WO | WO 2007/059248 | 5/2007 |
| WO | WO 2007/140535 | 12/2007 |
| WO | WO 2007/140536 | 12/2007 |
| WO | WO 2007/149553 | 12/2007 |
| WO | WO 2008/015449 | 2/2008 |
| WO | WO 2008/040846 | 4/2008 |
| WO | WO 2008/043365 | 4/2008 |
| WO | WO 2008/109694 | 9/2008 |
| WO | WO 2008/109699 | 9/2008 |
| WO | WO 2008/119029 | 10/2008 |
| WO | WO 2008/119031 | 10/2008 |
| WO | WO 2008/122082 | 10/2008 |
| WO | WO 2008/138340 | 11/2008 |

OTHER PUBLICATIONS

Partial International Search Report for International Application No. PCT/US2011/053540, dated Jan. 30, 2012, in 4 pages.

International Search Report for International Application No. PCT/US2011/053540, dated May 3, 2012, in 14 pages.

International Preliminary Report on Patentability for International Application No. PCT/US2011/053540, dated Apr. 2, 2013, in 9 pages.

* cited by examiner

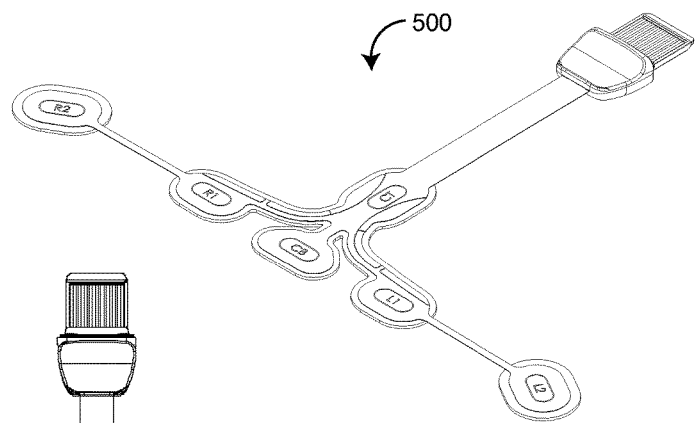
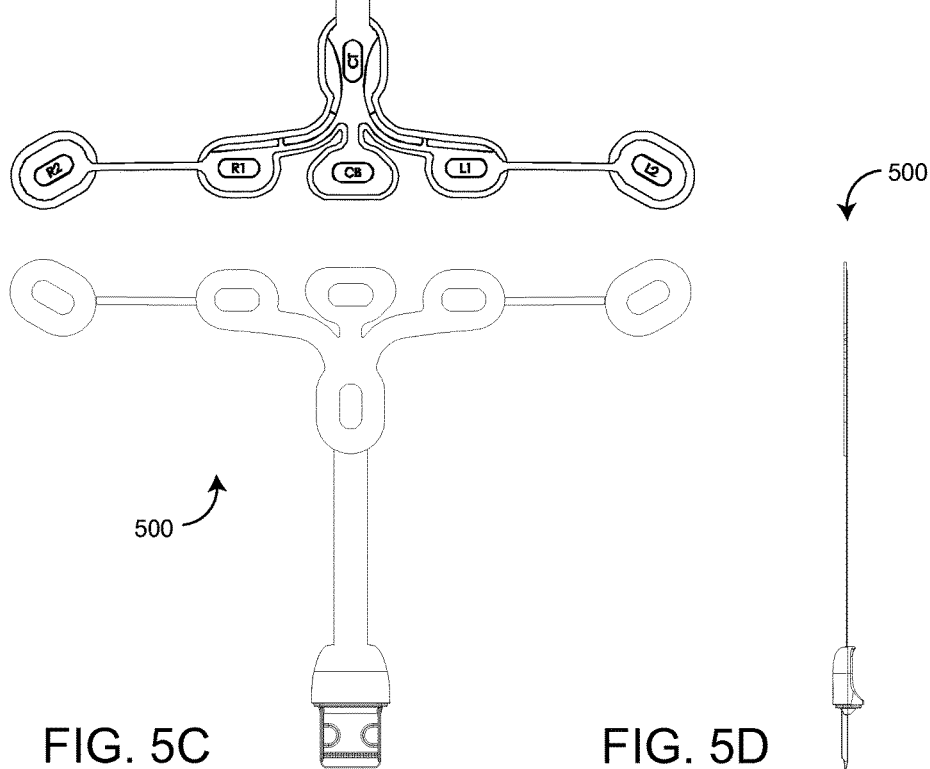
FIG. 5A  FIG. 5B
FIG. 5C  FIG. 5D

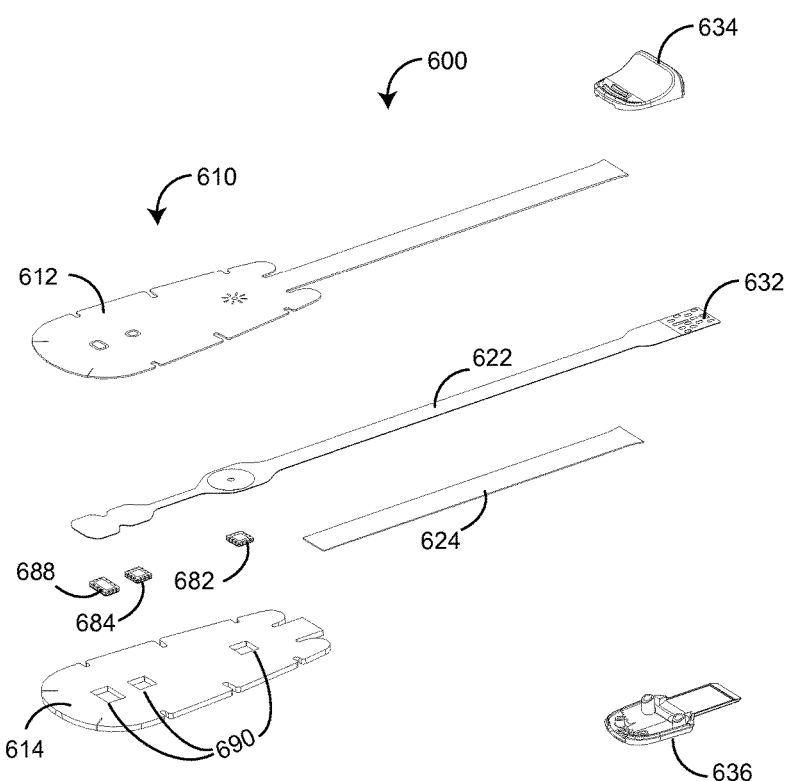
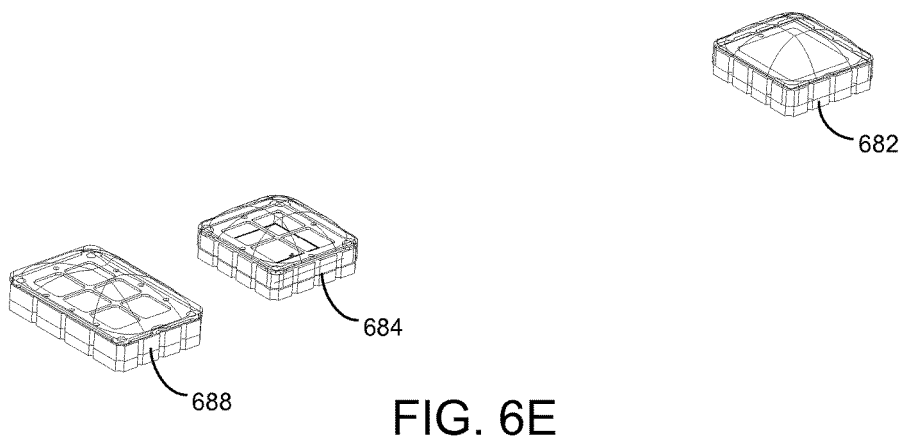
FIG. 6D
FIG. 6E

MODULAR PHYSIOLOGICAL SENSORS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The present application claims priority benefit under 35 U.S.C. § 119(e) to U.S. Provisional Patent Application Ser. No. 62/061,132 filed Oct. 7, 2014, titled Regional Oximetry-EEG Sensor. The above-cited provisional patent application is hereby incorporated in its entirety by reference herein.

FIELD OF THE DISCLOSURE

The present disclosure relates to physiological sensors. More specifically, the present disclosure relates to configurations for modular physiological sensors.

BACKGROUND

Pulse oximetry is a widely accepted noninvasive procedure for measuring the oxygen saturation level of arterial blood, an indicator of a person's oxygen supply. A typical pulse oximetry system utilizes an optical sensor attached to a fingertip to measure the relative volume of oxygenated hemoglobin in pulsatile arterial blood flowing within the fingertip. Oxygen saturation (SpO2), pulse rate and a plethysmograph waveform, which is a visualization of pulsatile blood flow over time, are displayed on a monitor accordingly.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated in their entireties by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated in their entireties by reference herein. Advanced pulse oximetry systems including Masimo SET® low noise optical sensors and read through motion pulse oximetry monitors for measuring SpO2, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad 8®, Rad 5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, Calif. (Cercacor) and all incorporated in their entireties by reference herein. Advanced blood parameter measurement systems include Masimo Rainbow® SET, which provides measurements in addition to SpO2, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY

The present disclosure relates to modular physiological sensors. In some situations in the clinical environment, it is necessary to use multiple physiological sensors in the same general measurement site of a patient. For example, the forehead, arm, hand, ear, and noes are all common areas where multiple physiological sensors may be used at the same time. The present disclosure provides for modular physiological sensors that are physically and/or electrically configured to share the measurement site for the comfort of the patient and to ensure proper operation of the sensors without interference from other sensors. The modular aspect is realized by providing outer housing shapes that generally conform to other physiological sensors; mounting areas for attachment of one sensor to another sensor; providing release liners on the overlapping sensor attachment areas; and/or providing notches, tabs or other mechanical features that provide for the proper placement and interaction of the sensors.

For example, regional oximetry (rO2), also referred to as tissue oximetry and cerebral oximetry, enables the continuous assessment of tissue oxygenation beneath a regional oximetry optical sensor. Regional oximetry helps clinicians detect regional hypoxemia that pulse oximetry alone can miss. In addition, the pulse oximetry capability in regional oximetry sensors can automate a differential analysis of regional to central oxygen saturation. Regional oximetry monitoring is as simple as applying regional oximetry sensors to any of various body sites including the forehead, forearms, chest, upper thigh, upper calf or calf, to name a few. Up to four sensors are connected to a conventional patient monitor via one or two regional oximetry pods. The pods advantageously drive the sensor optics, receive the detected optical signals, perform signal processing on the detected signals to derive regional oximetry parameters and communicate those parameters to a conventional patient monitor through, for example, standard USB ports. Although much of the present disclosure is explained by way of example with respect to EEG and rO2 sensors, it is to be understood that the modular configurations of the sensors can be applied to other types of physiological sensors and are not limited to EEG and rO2 sensors.

In some embodiments, an EEG sensor is advantageously shaped and marked on either side of a connector stem so as to allow regional oximetry (rO2) sensors to be placed in close proximity to the EEG sensor and so as to guide the proper placement of one or more rO2 sensors compactly next to the EEG sensor. The proper placement assistance and joint operation of the sensors provides for improved patient comfort and improved monitoring by ensuring the sensors do not interfere with each other. In some embodiments, the body shape of the EEG sensor is designed to the egg-shaped contours of the rO2 sensor heads. Further, markings on EEG contours correspond to notches on the rO2 sensor heads. These notches allow the rO2 sensor heads to conform to the curvature of a person's forehead. This integrated rO2-EEG sensor combination allows for measuring cerebral regional oximetry in conjunction with EEG parameters, such as depth of consciousness. The EEG sensor is applied first, as the EEG sensor electrodes have particular placement criteria. The EEG sensor markings, as described above, guide placement of the rO2 sensors, as these too require a particular placement for cerebral regional oximetry measurements. The EEG sensor skin-side is advantageously colored black so as to prevent the EEG sensor from reflecting the rO2 sensor-emitted light into the sensor detectors, which would degrade rO2 sensor performance.

In some embodiments, the rO2 sensors connect with a single rO2 pod and cable and the EEG sensor connects with a separate EEG pod and cable. In various other embodiments, a combination rO2-EEG sensor pod houses a single rO2 analog/digital signal processing board and a single EEG signal processing board and the rO2-EEG sensors each connect to the single rO2-EEG sensor pod.

One aspect of a brain analysis sensor is an EEG sensor having a stem, a left branch and a right branch. The left branch and the right branch extend generally perpendicularly from the stem so as to form a branch intersection. A plurality of right and left active electrodes are disposed along the left branch and the right branch. A ground electrode and reference electrode are disposed proximate the branch intersection. A mounting zone is disposed proximate the branch intersection for removable attachment of at least one regional oximetry (rO2) sensor.

In various embodiments, the mounting zone accommodates a regional oximetry sensor head having light emitting and light detecting elements. The mounting zone is marked with a curved line generally indicating a shape of the regional oximetry sensor head. The mounting zone comprises a release layer so that the regional oximetry sensor head removably attaches to the mounting zone. The regional oximetry sensor head has notches that accommodate a curved surface and the mounting zone has notch markings that generally align with the sensor head notches so as to aid regional oximetry sensor placement. The mounting zone is configured to removably attach two regional oximetry sensor heads. A first regional oximetry sensor head is mounted proximate a EEG sensor left branch and a second regional oximetry sensor head is mounted proximate a EEG sensor right branch.

Another aspect of a brain analysis sensor is a sensor method comprising mounting an EEG sensor on a forehead tissue site, mounting a first regional oximetry sensor on the forehead tissue site so as to at least partially overlap a first portion of the EEG sensor and mounting a second regional oximetry sensor on the forehead tissue site so as to at least partially overlap a second portion of the EEG sensor.

In various embodiments, the first portion and the second portion of the EEG sensor are marked for placement of the first and second regional oximetry sensors. A release liner is disposed on the first portion and the second portion for aiding removal of the regional oximetry sensors. The shape of the marked portions conform to shape of the regional oximetry sensors. The marked portions also designate the location of notches on head portions of the regional oximetry sensors.

A further aspect of a brain analysis sensor is an electrical sensor means for passively measuring an EEG signal, an optical sensor means for detecting an oxygen saturation and a placement means for at least partial overlapping the electrical sensor means and the optical sensor means on a tissue site. In an embodiment, the placement means comprises a marking means for designating the partial overlapping. In an embodiment, the marking means comprises at least a partial duplication of the optical sensor means shape on the electrical sensor means.

Regional oximetry sensors and pods are disclosed in U.S. patent application Ser. No. 14/507,620, titled Regional Oximetry Sensor, filed Oct. 6, 2014 by Masimo Corporation, Irvine, Calif. and incorporated in its entirety by reference herein. An EEG sensor and monitor are disclosed in U.S. patent application Ser. No. 14/470,819, titled Depth of Consciousness Monitor, filed Aug. 27, 2014 by Masimo Corporation, Irvine, Calif. and incorporated in its entirety by reference herein.

BRIEF DESCRIPTION OF THE DRAWINGS

FIGS. 5A-E are top, perspective, bottom, side and exploded perspective views, respectively, of an rO2-configured EEG sensor; and FIGS. 6A-E are top, side, bottom and exploded top perspective views, respectively, of a rO2 sensor and an enlarged perspective view of rO2 sensor optical elements.

DETAILED DESCRIPTION OF THE PREFERRED EMBODIMENT

Figure 1:
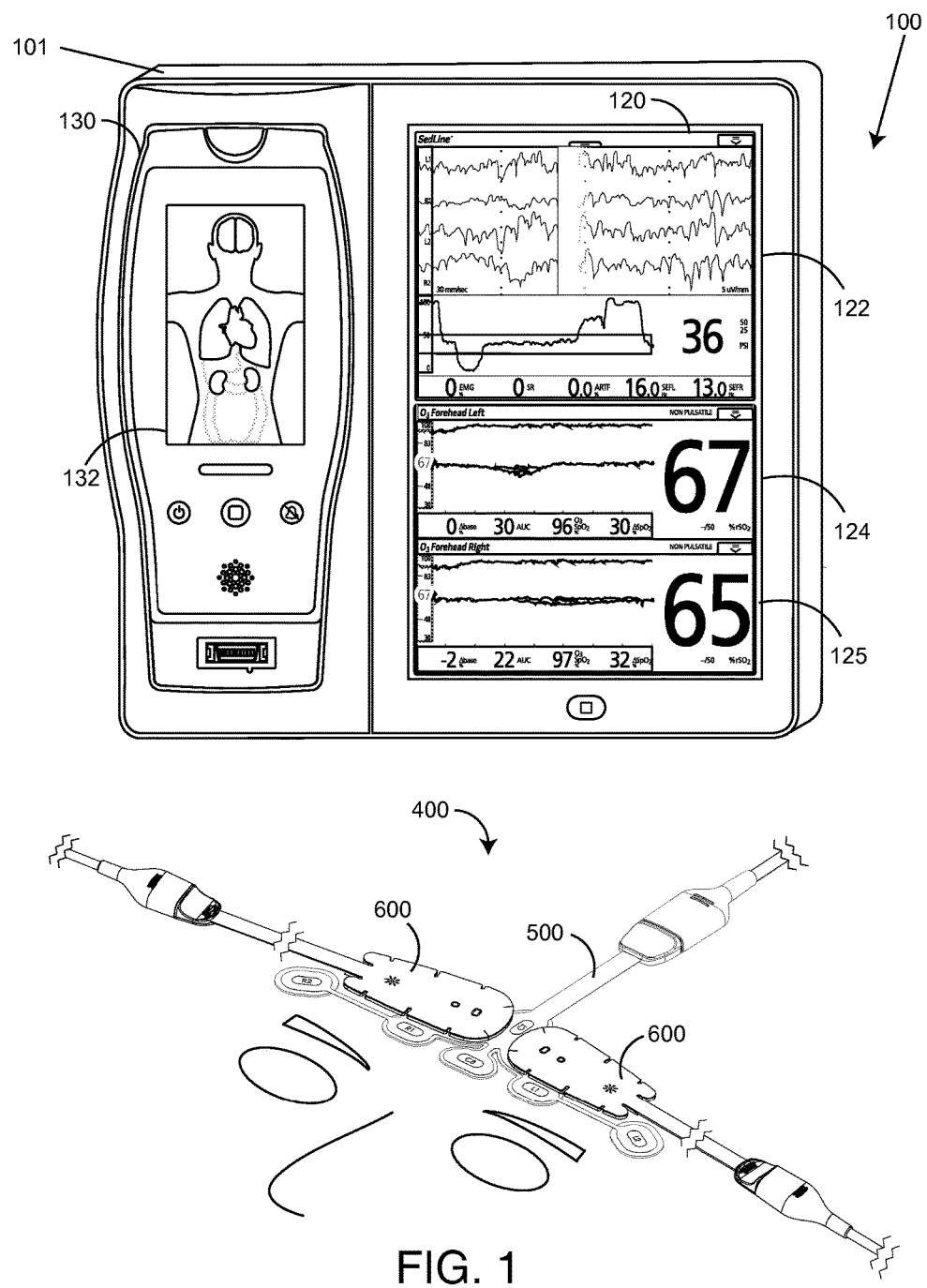
FIG. 1 is a perspective view of a brain analysis system having an advantageous modular brain analysis sensor applied to a forehead site and in communications with a physiological monitor for generating simultaneous electroencephalogram (EEG) and left and right forehead regional oximetry (rO2) parameter values and waveforms.

FIG. 1 illustrates a brain analysis system 100 having an advantageous modular brain analysis sensor 400 applied to a forehead tissue site in communications with a physiological monitor 101 for measuring and generating simultaneous electroencephalogram (EEG) and left and right forehead regional oximetry (rO2) parameter values and waveforms. The modular brain analysis sensor 400 can be advantageously assembled and placed within a limited-area forehead site. Also, the rO2 components 600 and EEG component 500 can be advantageously purchased, stocked and used separately and individually, saving hospital and medical care center costs over other, more specialized brain analysis sensors not having separately useable regional oximetry and EEG sensor functions. The same cost savings is realized by modular designs for any and all types of physiological monitoring sensors.

As shown in FIG. 1, the brain analysis sensor 400 has an EEG sensor (FIGS. 4-5) that co-mounts dual regional oximetry (rO2) sensors. Each of these sensor functions are in communications with a physiological monitor 101 having a main display 120 and a (removable) handheld monitor 130 having a handheld 132. The main display 120 provides EEG waveforms and parameter values 122 in addition to forehead left 124 and forehead right 125 regional oximeter waveforms and parameters. The handheld display 132 provides a 3-D man graphic displaying green, yellow and red organ symbols (brain, lung and kidneys) corresponding to EEG and/or rO2 parameter values. Similar displays can be provided for other physiological parameters as well.

Also shown in FIG. 1, a modular brain analysis sensor 400 advantageously has dual rO2 sensors 600 that overlap right- and left-side portions of a specially-configured and marked (rO2-configured) EEG sensor 500 so as to compactly fit these modular sensors 500, 600 within a limited-space forehead site, as described in detail with respect to FIGS. 2-4, below. An rO2-configured EEG sensor 500 is described in detail with respect to FIGS. 5A-E, below. An regional oximetry sensor 600 is described in detail with respect to FIGS. 6A-E, below.

Further shown in FIG. 1, in an EEG screen portion 122, the physiological monitor 101 display 120 shows 4 simultaneous EEG channels along with a patient state index (PSI) readout versus time so as to enable continuous assessment of both sides of the brain, such as for improved anesthetic management. In addition, forehead left 124 and forehead right 125 regional oximetry waveforms and readouts enable monitoring of brain tissue oxygen saturation and detect regional hypoxemia.

Figures 2, 3:
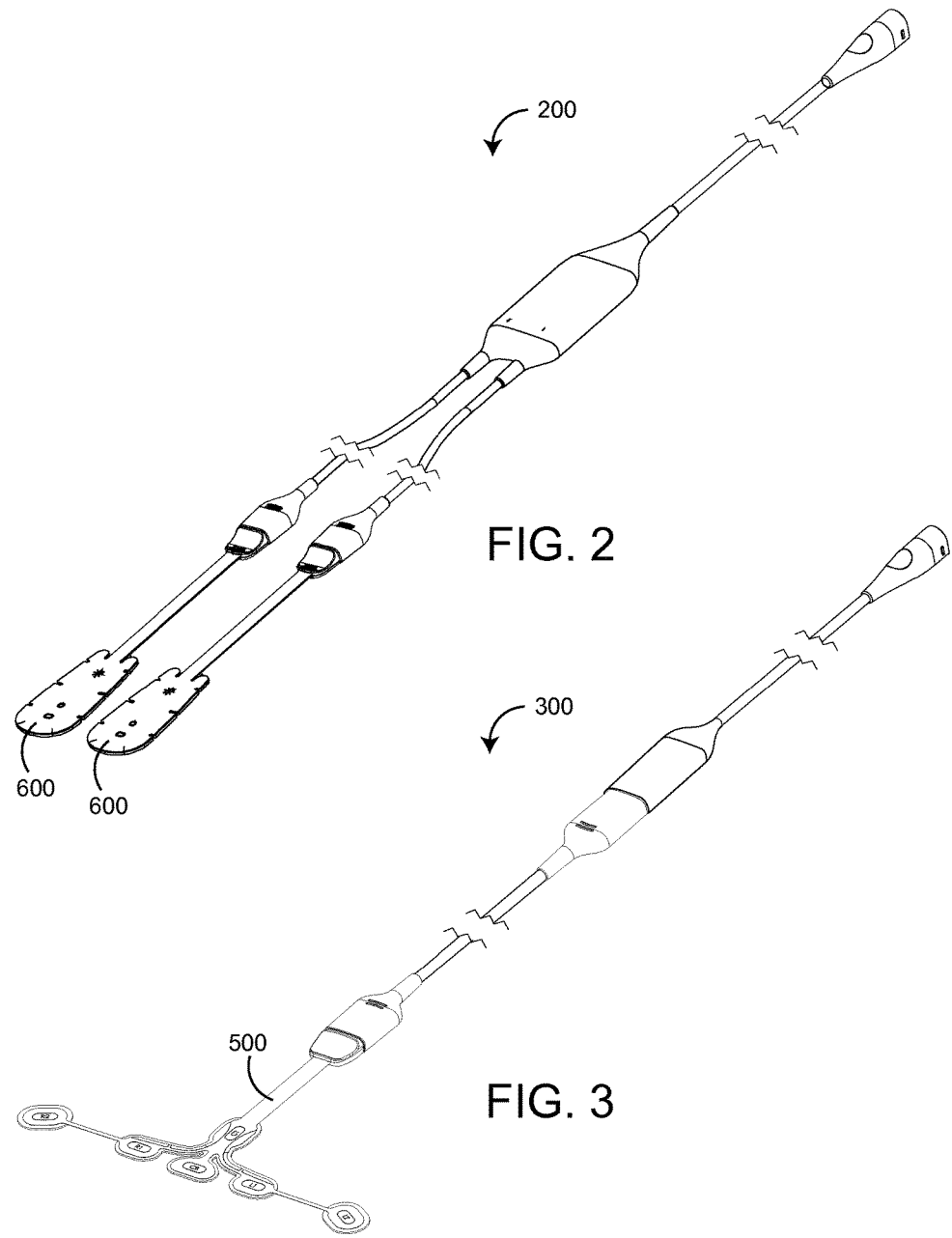
FIGS. 2-3 are perspective views, respectively, of a regional oximetry (rO2) sensor and cable assembly and an EEG sensor and cable assembly.

FIGS. 2-3 illustrate, respectively, a regional oximetry (rO2) sensor and cable assembly and an EEG sensor and cable assembly. As shown in FIG. 2, the regional oximetry (rO2) cable assembly 200 interconnects dual rO2 sensors 600 to a physiological monitor 101 (FIG. 1). The rO2 cable assembly has dual sensor connectors at a sensor end, a monitor connector (MOC9) at a monitor end and a rO2 pod mounted between and in communications with the sensor connectors and the monitor connector. Also shown in FIG. 2, the rO2 pod has regional oximetry analog and digital boards. The analog board communicates with one or more of the regional oximetry sensors 600. The digital board enables the pod to perform the sensor communications and signal processing functions of a conventional patient monitor. This allows pod-derived regional oximetry parameters to be displayed on a variety of monitors ranging from simple display devices to complex multiple parameter patient monitoring systems.

As shown in FIG. 3, the EEG cable assembly 300 interconnects an EEG sensor 500 to a physiological monitor 101 (FIG. 1). The EEG cable assembly 300 has an EEG connector at a sensor end, a monitor connector (MOC9) at a monitor end and a EEG pod mounted between and in communications with the sensor connectors and the monitor connector.

Figure 4A:
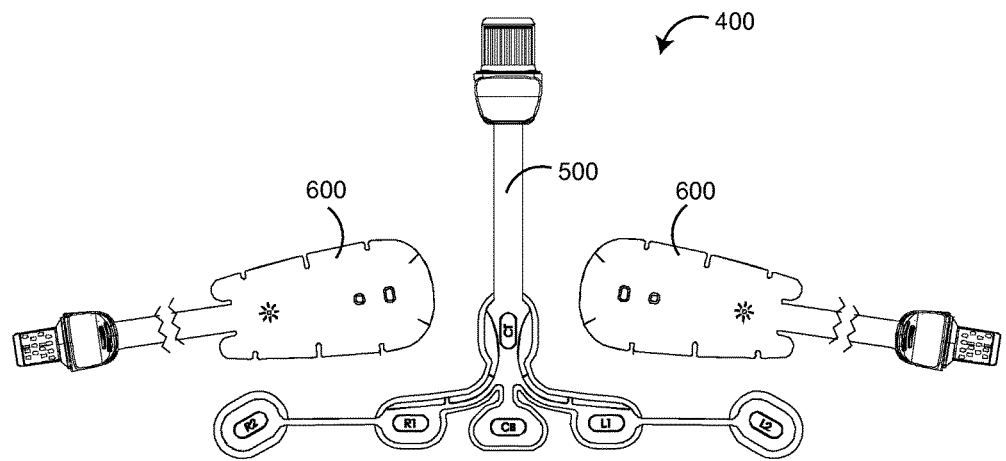
FIGS. 4A-B are an exploded plan view (FIG. 4A) and a detailed plan view (FIG. 4B), respectively, of a modular brain analysis sensor having an advantageous keyed mounting zone (shaded) for precise, overlaid placement of dual rO2 sensors on an rO2-configured EEG sensor.
Figure 4B:
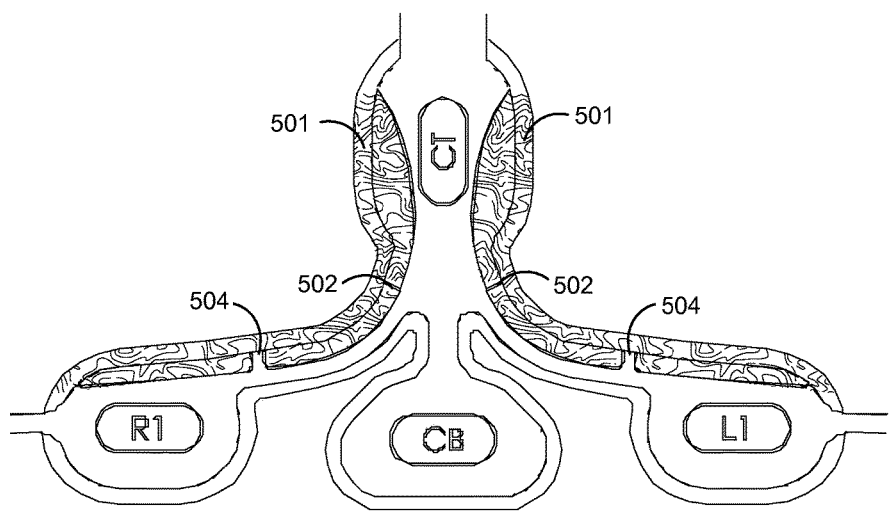

FIGS. 4A-B illustrate a modular brain analysis sensor 400 having advantageous keyed mounting zones 501 (shaded) for precise, overlaid placement of dual rO2 sensors on an EEG sensor. In particular, the EEG sensor 500 has two mounting zones 501, one on either side of the interconnected between the EEG electrodes and the EEG sensor connector. Each mounting zone accommodates one of two rO2 sensors (see FIG. 1 and FIG. 4A). Further, each mounting zone 501 (FIG. 4B) is shaped and printed to conform to a top and side portion of an rO2 sensor head 610 (FIGS. 6A-D). Further, each mounting zone has printed notches 502, 504 corresponding to actual notches in the rO2 sensor heads 610 (FIG. 6A) that accommodate curved tissue site surfaces. These printed notches 502, 504 further aid in the alignment of rO2 sensors to the mounting zones 501.

Figure 5E:
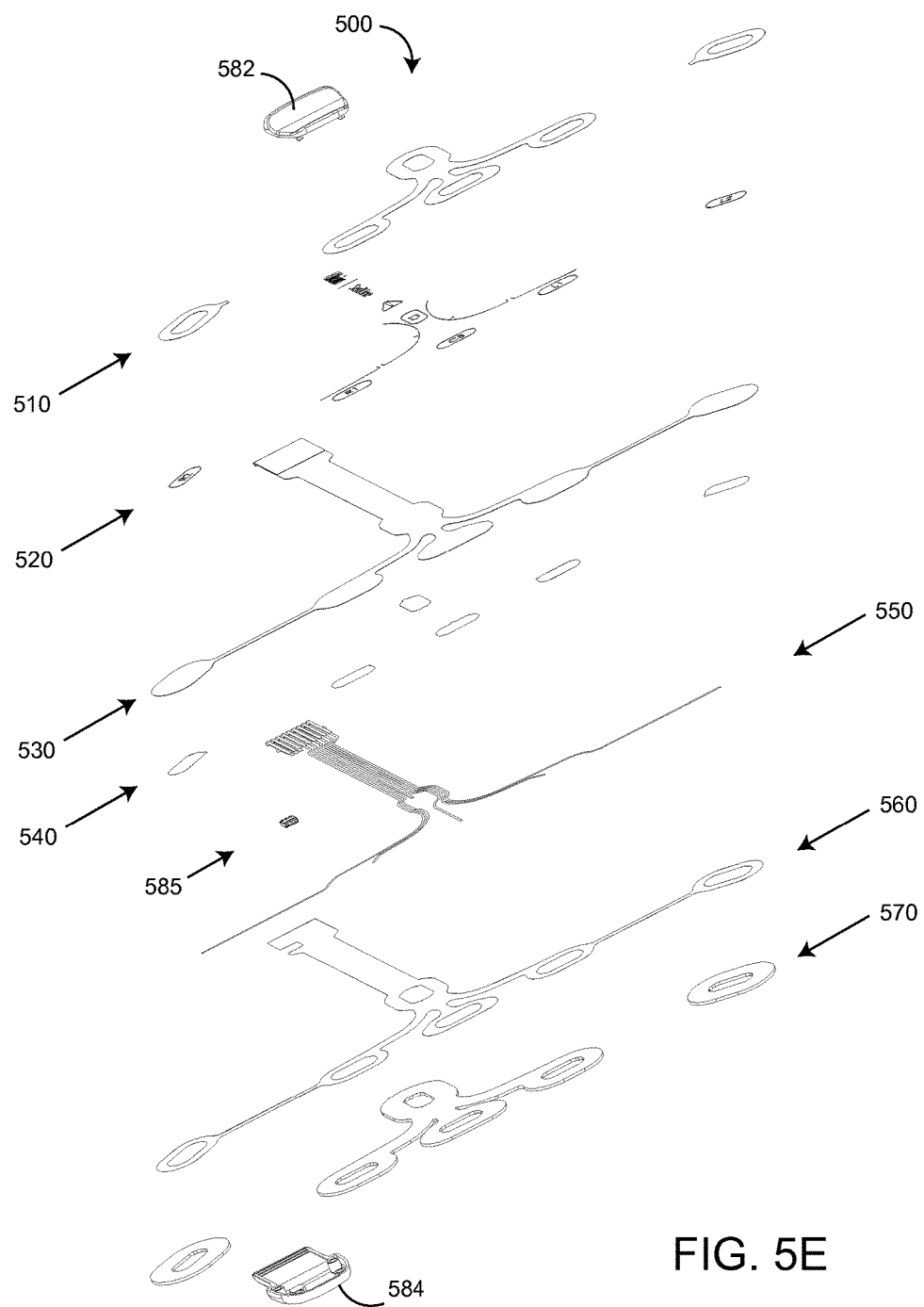
Figure 6A:
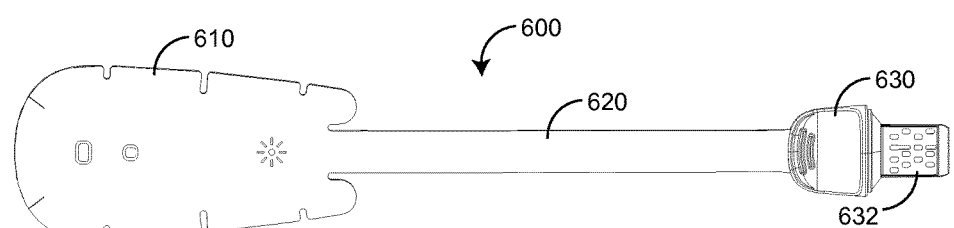
Figure 6B:
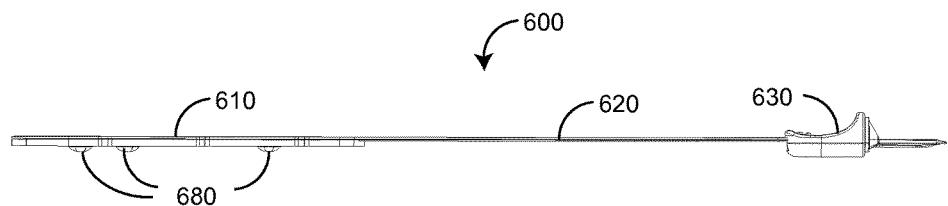
Figure 6C:
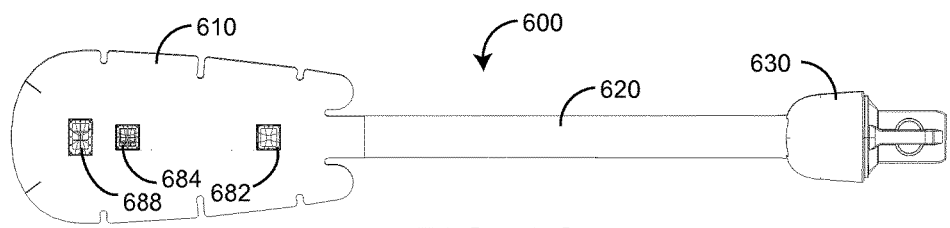

FIGS. 5A-E further illustrate an rO2 configured EEG sensor 500 having a generally "T" shape with six electrodes including two right electrodes R1, R2; two left electrodes L1, L2; a ground electrode CB and a reference electrode CT. As shown in FIG. 5A, the R1, R2, L1, L2 and CB electrodes are disposed across the horizontal top of the "T." The reference electrode CT is disposed on the vertical middle of the "T." The advantageous mounting zone 501 (FIG. 4B) is disposed on either side of the vertical middle of the "T" proximate the horizontal top of the "T."

As shown in FIG. 5E, the EEG sensor 500 has multiple layers including a release liner 510 that allows an attached rO2 sensor 600 (FIG. 1) to be removed and repositioned; artwork 520 including rO2 sensor positioning lines 502 (FIG. 4B); a polyester substrate 530; silver pads 540 (electrodes); silver ink traces 550; a dielectric layer 560 that isolates and protects the traces 550 and a foam pad 570 that contacts a user's skin. The EEG sensor connector includes a top shell 582 and a bottom shell 584. An information element 585 mechanically and electrically connects to the trace layer 550.

FIGS. 6A-E further illustrate a rO2 sensor and its optical elements having a sensor head 610, a stem 620 and a connector 630. The sensor head 610 houses an emitter 682, a near-field detector 684 and a far-field detector 688 within a layered tape having a top side (FIG. 6A) and an adhesive bottom side (FIG. 6C) disposed on a release liner. The release liner is removed so as to adhere the bottom side to a skin surface. The emitter 682 and detectors 684,688 have lens that protrude from the bottom side (FIG. 6E) advantageously providing a robust optics-skin interface. The top side has printed emitter/detector indicators so as to aid precise sensor placement on a patient site. A connector 630 terminates the interconnect 620 at the connector contacts 632.

Also shown in FIG. 6D, a sensor head assembly 610 has a face tape 612, a flex circuit 622, a stem tape 620, a base tape 624, a connector top 634 and a connector base 636. The face tape 612 and base tape 622 encase the flex circuit 622 and corresponding emitter and detectors 682-688.

A modular physiological sensor has been disclosed in detail in connection with various embodiments. These embodiments are disclosed by way of examples only and are not to limit the scope of this disclosure and the claims herein. One of ordinary skill in art will appreciate many variations and modifications. It should be understood specifically that the present mounting zones, tabs, relative shapes and modular configuration can be applied to other physiological sensors including, for example, ear, nose, hand, harm, and/or chest sensors or any other types of physiological sensors where the sensors are configured to jointly measure the same measurement site of a patient.

What is claimed is:

1. A modular physiological sensor comprising:
an electroencephalogram (EEG) sensor comprising a stem, a left branch and a right branch;
the left branch and the right branch extending generally perpendicularly from the stem so as to form a branch intersection, wherein the branch intersection includes a left corner defined by an intersection of the left branch and the stem of the EEG sensor and a right corner defined by an intersection of the right branch and the stem of the EEG sensor;

a plurality of EEG electrodes disposed along the left branch and the right branch;
a ground electrode and a reference electrode disposed proximate the branch intersection;
a first mounting zone extending outwardly along an edge of the left corner of the branch intersection and configured for removable attachment of a first regional oximetry (rO2) sensor, said first rO2 sensor comprising a first edge including a first outline shape; and
a second mounting zone extending outwardly along an edge of the right corner of the branch intersection and configured for removable attachment of a second rO2 sensor, said second rO2 sensor comprising a second edge including a second outline shape;
wherein the first mounting zone is shaped to match at least a portion of said first outline shape; and
wherein the second mounting zone is shaped to match at least a portion of said second outline shape.

2. The modular physiological sensor according to claim 1, wherein the first mounting zone accommodates a first rO2 sensor head having a first pair of light emitting and light detecting elements and the second mounting zone accommodates a second rO2 sensor head having a second pair of light emitting and light detecting elements.

3. The modular physiological sensor according to claim 2, wherein the first mounting zone is marked with a first curved line generally indicating a first shape of the first rO2 sensor head, and wherein the second mounting zone is marked with a second curved line generally indicating a second shape of the second rO2 sensor head.

4. The modular physiological sensor according to claim 3, wherein the first mounting zone comprises a first release layer so that the first rO2 sensor head removably attaches to the first mounting zone, and wherein the second mounting zone comprises a second release layer so that the second rO2 sensor head removably attaches to the second mounting zone.

5. The modular physiological sensor according to claim 4, wherein:
the first rO2 sensor head has a first plurality of notches that accommodate a first curved surface and the second rO2 sensor head has a second plurality of notches that accommodate a second curved surface;
the first mounting zone has a first plurality of notch markings that generally align with the first plurality of notches so as to aid placement of the first rO2 sensor and the second mounting zone has a second plurality of notch markings that generally align with the second plurality of notches so as to aid placement of the second rO2 sensor.

6. The modular physiological sensor according to claim 2, wherein a skin-side surface of the EEG sensor is colored black so as to prevent the EEG sensor from reflecting light emitted from the first and second rO2 sensor heads.

7. The modular physiological sensor according to claim 2, wherein the first and second rO2 sensor heads are egg-shaped.

8. A brain analysis sensing method comprising:
mounting an electroencephalogram (EEG) sensor on a forehead tissue site, the EEG sensor including a stem, a left branch, and a right branch, wherein the left branch and the right branch extend generally perpendicularly from the stem so as to form a branch intersection, the branch intersection including a left corner defined by the intersection of the left branch and the stem of the EEG sensor and a right corner defined by the intersection of the right branch and the stem of the EEG sensor;
mounting a first regional oximetry sensor on the forehead tissue site so as to at least partially overlap a first portion of the EEG sensor, the first portion extending outwardly along an edge of the left corner of the branch intersection, the first regional oximetry sensor comprising a first edge including a first outline shape; and
mounting a second regional oximetry sensor on the forehead tissue site so as to at least partially overlap a second portion of the EEG sensor, the second portion extending outwardly along an edge of the right corner of the branch intersection, the second regional oximetry sensor comprising a second edge including a second outline shape;
wherein the first portion of the EEG sensor is shaped to match at least a portion of said first outline shape; and
wherein the second portion of the EEG sensor is shaped to match at least a portion of said second outline shape.

9. The brain analysis sensing method according to claim 8, further comprising marking the first portion and the second portion on the EEG sensor for placement of the first and second regional oximetry sensors.

10. The brain analysis sensing method according to claim 9, further comprising providing a release liner on the first portion and the second portion for aiding removal of the regional oximetry sensors.

11. The brain analysis sensing method according to claim 10, wherein the first and second regional oximetry sensors are egg-shaped.

12. The brain analysis sensing method according to claim 11, further comprising indicating on the marked first portion and the marked second portion the location of notches on head portions of the regional oximetry sensors.

13. A brain analysis sensor comprising:
an electrical sensor configured to passively measure an EEG signal, the electrical sensor comprising a generally T shape including a first mounting zone positioned along an edge of a left side of a vertical middle of the T shape and a second mounting zone positioned along an edge of a right side of the vertical middle of the T shape;
an optical sensor configured to detect an oxygen saturation; and
a placement guide configured to aid with the partial overlapping of a first portion of the optical sensor having a first outline shape atop either the first mounting zone or the second mounting zone of the electrical sensor, wherein at least one of the first mounting zone and the second mounting zone is shaped to match at least a portion of said first outline shape; and
wherein a second portion of the optical sensor is configured to attach to a skin surface.

14. The brain analysis sensor according to claim 13, wherein the placement guide comprises a marking configured to designate the partial overlapping.

15. The brain analysis sensor according to claim 14, wherein the marking comprises at least a partial duplication of the optical sensor shape on the electrical sensor.

16. The modular physiological sensor according to claim 13, wherein the optical sensor is egg-shaped.

17. A modular physiological sensor comprising:
a first electronics useful for measuring a first physiological parameter;
a mounting system configured to mount the first electronics to a patient measurement site, wherein the mounting system comprises a stem, a left branch, and a right branch, the left branch and the right branch extending in opposite directions along a transverse axis generally perpendicular to a longitudinal axis running along a centerline of the stem; and a first mounting zone on the mounting system located on a left side of the stem of the mounting system, the first mounting zone extending away from an edge of the left branch in a first direction substantially parallel to the longitudinal axis of the stem and extending away from an edge of the stem in a second direction substantially parallel to the transverse axis, wherein the first mounting zone is shaped and physically configured to receive and position a first outline shape of a first physiological sensor; and a second mounting zone on the mounting system located on a right side of the stem of the mounting system, the second mounting zone extending away from an edge of the right branch in a third direction substantially parallel to the longitudinal axis of the stem and extending away from an edge of the stem in a fourth direction substantially parallel to the transverse axis, wherein the second mounting zone is shaped and physically configured to receive and position a second outline shape of a second physiological sensor.

18. The modular physiological sensor according to claim 17, wherein the first and second physiological sensors comprise electronics that are different from the first electronics, and wherein the first and second physiological sensors are configured for measuring a physiological parameter different from the first physiological parameter.

19. The modular physiological sensor according to claim 17, wherein at least one of the first and second mounting zones are marked with a line generally indicating the first outline shape of the first physiological sensor or the second outline shape of the second physiological sensor.

20. The modular physiological sensor according to claim 17, wherein the first and second mounting zones each comprise a release layer so that the first and second physiological sensors removably attach to the first and second mounting zones.

21. The modular physiological sensor according to claim 17, wherein:

the first physiological sensor includes a first plurality of notches and the second physiological sensor includes a second plurality of notches; and the first mounting zone includes a first plurality of notch markings that generally align with the first plurality of notches in order to aid sensor placement, and the second mounting zone includes a second plurality of notch markings that generally align with the second plurality of notch markings in order to aid sensor placement.

22. The modular physiological sensor according to claim 17, wherein the first and second physiological sensors are egg-shaped.

* * * * *